United States Patent
Otagiri et al.

(10) Patent No.: US 11,162,087 B2
(45) Date of Patent: Nov. 2, 2021

(54) BETA-GLUCOSIDASE, ENZYME COMPOSITION INCLUDING SAME, AND METHOD FOR MANUFACTURING SUGAR SOLUTION USING SAME

(71) Applicants: RIKEN, Wako (JP); TORAY INDUSTRIES, INC., Tokyo (JP)

(72) Inventors: Masato Otagiri, Wako (JP); Shigeharu Moriya, Wako (JP); Masahiro Yuki, Wako (JP); Moriya Ohkuma, Wako (JP); Haruka Saito, Kamakura (JP); Shingo Hiramatsu, Kamakura (JP); Chiaki Yamada, Kamakura (JP); Katsushige Yamada, Kamakura (JP)

(73) Assignees: RIKEN, Wako (JP); TORAY INDUSTRIES, INC., Tokyo (JP)

( * ) Notice: Subject to any disclaimer, the term of this patent is extended or adjusted under 35 U.S.C. 154(b) by 0 days.

(21) Appl. No.: 16/642,551

(22) PCT Filed: Aug. 29, 2018

(86) PCT No.: PCT/JP2018/031910
§ 371 (c)(1),
(2) Date: Feb. 27, 2020

(87) PCT Pub. No.: WO2019/044887
PCT Pub. Date: Mar. 7, 2019

(65) Prior Publication Data
US 2021/0079435 A1    Mar. 18, 2021

(30) Foreign Application Priority Data
Aug. 30, 2017 (JP) .............................. JP2017-165787

(51) Int. Cl.
*C12N 9/26* (2006.01)
*C12P 19/14* (2006.01)
(Continued)

(52) U.S. Cl.
CPC ............ *C12N 9/2445* (2013.01); *C12P 19/14* (2013.01); *C12N 1/16* (2013.01); *C12N 15/80* (2013.01); *C12Y 302/01021* (2013.01)

(58) Field of Classification Search
CPC ............................... C12N 9/2445; C12P 19/14
See application file for complete search history.

(56) References Cited

FOREIGN PATENT DOCUMENTS

| | | |
|---|---|---|
| JP | 2003-70475 A | 3/2003 |
| JP | 2010-516296 A | 5/2010 |
| WO | WO 2008/095033 A2 | 8/2008 |

OTHER PUBLICATIONS

Inoue. A0A0E9LZ60_9BACT. UnitProtKB Database. 2015.*

(Continued)

*Primary Examiner* — Yong D Pak
(74) *Attorney, Agent, or Firm* — Birch, Stewart, Kolasch & Birch, LLP

(57) ABSTRACT

The object of the present invention is to separate and provide a β-glucosidase gene having the effect of efficiently promoting saccharification in hydrolysis of cellulose-containing biomass from a hardly culturable symbiotic protist community of *Coptotermes formosanus*, and the present invention specifically relates to β-glucosidase derived from a protist of the genus *Pseudotrichonympha* consisting of the amino acid sequence represented by SEQ ID NO: 1.

7 Claims, 5 Drawing Sheets

Specification includes a Sequence Listing.

(51) Int. Cl.
  *C12N 9/42* (2006.01)
  *C12N 1/16* (2006.01)
  *C12N 15/80* (2006.01)

(56) References Cited

OTHER PUBLICATIONS

Studer. Residue mutations and their impact on protein structure and function: detecting beneficial and pathogenic changes. Biochem. J. (2013) 449, 581-594.*
Andríc et al., "Reactor design for minimizing product inhibition during enzymatic lignocellulose hydrolysis: I. Significance and mechanism of cellobiose and glucose inhibition on cellulolytic enzymes", Biotechnology Advances, vol. 28, (2010), p. 308-324.
International Search Report, issued in PCT/JP2018/031910, PCT/ISA/210, dated Nov. 13, 2018.
Messner et al., "Evidence for a single, specific β-glucosidase in cell walls from Trichoderma reesei QM9414", Enzyme Microb. Technol., Sep. 1990, vol. 21, p. 685-690.
Written Opinion of the International Searching Authority, issued in PCT/JP2018/031910, PCT/ISA/237, dated Nov. 13, 2018.

\* cited by examiner

Fig. 5

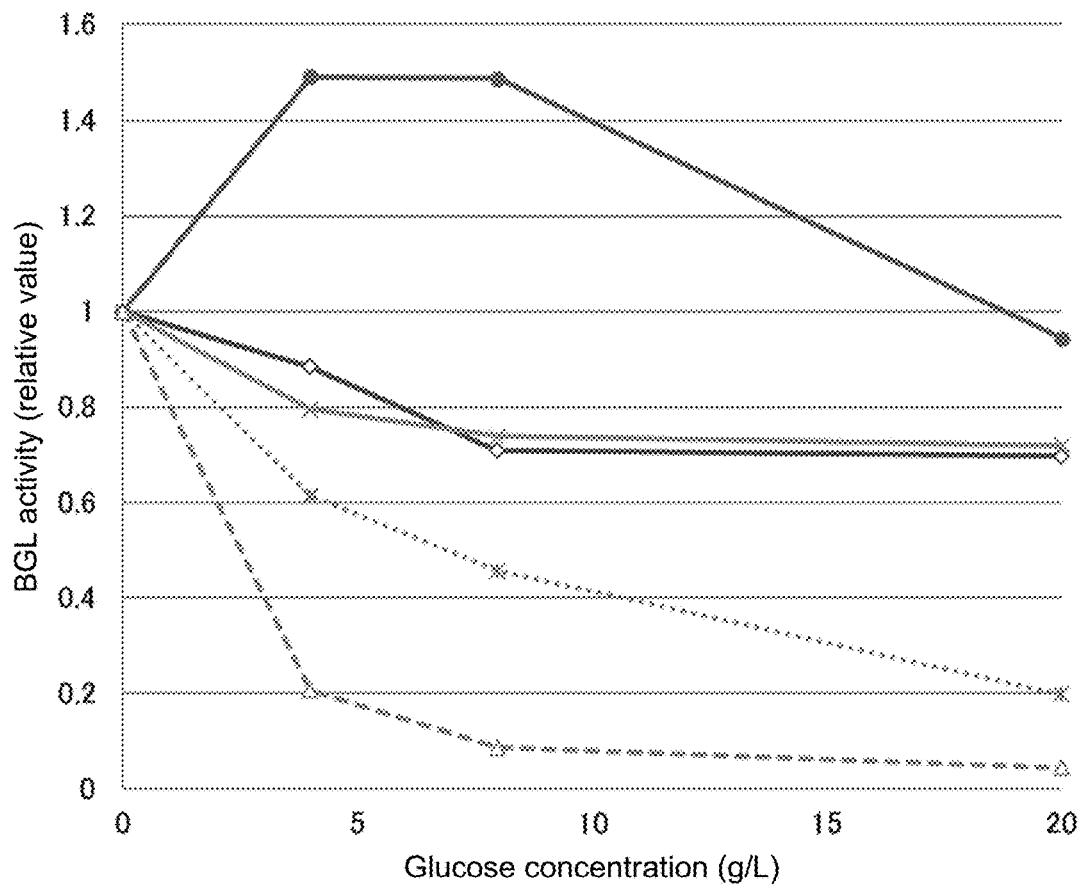

—◆— β-glucosidase of the present invention (SEQ ID NO: 1)
: β-glucosidase derived from a protist of the genus Pseudotrichonympha and the genus Trichoderma filamentous fungus-derived cellulase —◇— β-glucosidase mutant 1 of the present invention (SEQ ID NO: 6)
: Cell-free extract of β-glucosidase mutant gene transformed E. coli —✳— β-glucosidase mutant 2 of the present invention (SEQ ID NO: 8)
: Cell-free extract of β-glucosidase mutant gene transformed E. coli ··✳·· Comparative Example 1: β-glucosidase derived from the genus Aspergillus filamentous fungus (enzyme composition containing the genus Aspergillus filamentous fungus-derived β-glucosidase and the genus Trichoderma filamentous fungus-derived cellulase)

-- △ -- Comparative control: BGL derived from the genus Trichoderma filamentous fungus (the genus Trichoderma filamentous fungus-derived cellulase alone)

BETA-GLUCOSIDASE, ENZYME COMPOSITION INCLUDING SAME, AND METHOD FOR MANUFACTURING SUGAR SOLUTION USING SAME

TECHNICAL FIELD

The present invention relates to a novel β-glucosidase, an enzyme composition containing the β-glucosidase, and a method for producing a sugar solution from cellulose-containing biomass using them.

BACKGROUND ART

Vigorous studies have been made at home and abroad on attempts to fermentatively produce a biofuel or a biopolymer raw material as an alternative resource to crude oil by degrading renewable cellulose-containing biomass and using a sugar obtained therefrom.

Although there are various methods for saccharifying cellulose, enzymatic saccharification methods having smaller amount of energy usage and a higher sugar yield have become main stream for development. A plurality of enzyme species is involved in enzymatic degradation of cellulose, and they are roughly classified into three species, cellobiohydrolase, endoglucanase and β-glucosidase. Cellobiohydrolase is an enzyme that is characterized by hydrolyzing cellulose from its end portion and is capable of degrading a crystalline region of cellulose. On the other hand, endoglucanase is an enzyme that is characterized by hydrolyzing a cellulose molecular chain from its inner region and promotes a decrease in the molecular weight through cellulose degradation.

β-glucosidase is an enzyme that mainly degrades cellobiose of two sugars produced by β-1,4 bond of glucose and catalyzes the production of glucose as a final degradation product, and it is an essential enzyme in order to sufficiently obtain glucose useful as a raw material for fermentation. In addition, it is known that reaction inhibition to cellobiohydrolase or endoglucanase is caused by accumulation of cellobiose produced by cellulose degradation. That is, β-glucosidase is able to significantly reduce accumulation of cellobiose produced by cellulose degradation, and thus, it has an effect of significantly improving the cellulose degradation efficiency.

Meanwhile, as a microorganism to produce cellulase, filamentous fungi are known. Among filamentous fungi, the genus *Trichoderma* is known as extracellularly producing large amounts of endo- and exo-cellulase in a culture solution. *Trichoderma*-derived cellulase is the most frequently used for enzymatic degradation of cellulose-containing biomass. However, part of β-glucosidase produced by *Trichoderma* is localized in the bacterial cell wall (Non Patent Literature 1), and cellulase prepared from a *Trichoderma* culture solution has had a drawback in that the amount and the activity of β-glucosidase contained therein were not adequate. In addition, it is known that many filamentous fungi-derived β-glucosidases suffer from inhibition on the β-glucosidase activity by glucose; and then, in saccharifying clullose-containing biomass, they have a drawback in that glucose produced in a saccharified reaction solution by cellulose degradation causes β-glucosidase activity inhibition, thereby preventing an increase in the accumulated amount of glucose in the saccharified reaction solution (Non Patent Literature 2).

Thus, there is a demand for a good β-glucosidase having an effect of efficiently implementing saccharification in the hydrolysis of cellulose-containing biomass, and isolation of microorganism-derived β-glucosidase has been conventionally carried out.

It has been known that a symbiotic protist community of termites using only wood as a nutrient source has an extremely high cellulose degradation efficiency. However, analyses on the symbiotic protists have not been progressed because they are hardly culturable. Even recent years have witnessed a small volume of studies on symbiotic protists and cellulase thereof (Patent Literature 1), and no case has been found so far on obtainment of a β-glucosidase gene derived from a symbiotic protist of termites.

CITATION LIST

Patent Literature

Patent Literature 1: JP Patent Publication No. 2003-70475

Non Patent Literature

Non Patent Literature 1: Messner, R et al., "Evidence for a single, specific β-glucosidase in cell wall from Tricoderma QM9414," Enzyme Microb. Technol., 1990, Vol. 21, pages 685 to 690

Non Patent Literature 2: Andric, P, et al., "Reactor design for minimizing product inhibition during enzymatic lignocellulose hydrolysis: I. Significance and mechanism of cellobiose and glucose inhibition on cellulolytic enzymes," Biotechnol. Adv., 2010, Vol. 28, pages 308 to 324

SUMMARY OF INVENTION

Technical Problem

The problem to be solved by the present invention is to separate and provide, from a hardly culturable symbiotic protist community of *Coptotermes formosanus*, a β-glucosidase gene having an effect of efficiently promoting saccharification in hydrolysis of cellulose-containing biomass.

Solution to Problem

To solve the above problem, the present inventors have made intensive studies and found that a novel β-glucosidase derived from a protist of the genus *Pseudotrichonympha* can be applied to the degradation of cellulose-containing biomass by: observing an expression gene from a small amount of RNA of a hardly culturable symbiotic protist of *Coptotermes formosanus* using single-cell transcriptome analysis; obtaining a β-glucosidase candidate sequence from sequence information of an obtained cDNA library; investigating effects of a transformant containing the β-glucosidase candidate sequence in the β-glucosidase activity and saccharification of cellulose-containing biomass; and selecting a sequence having β-glucosidase activity, thereby completing the present invention.

That is, the present invention includes the following.

[1] A polypeptide of any one of the following (A) to (C):

(A) a polypeptide that is an amino acid sequence represented by SEQ ID NO: 1;

(B) a polypeptide obtained by substituting, deleting, inserting and/or adding one or several amino acids in the amino acid sequence represented by SEQ ID NO: 1 and having β-glucosidase activity; and (C) a polypeptide having at least 70% sequence identity with the amino acid sequence represented by SEQ ID NO: 1 and having β-glucosidase activity.

[2] A polynucleotide that is any one of the following (a) to (d):

(a) a polynucleotide consisting of a nucleotide sequence represented by SEQ ID NO: 2;

(b) a polynucleotide consisting of a nucleotide sequence obtained by substituting, deleting, inserting and/or adding one or several nucleotides in the nucleotide sequence represented by SEQ ID NO: 2 and encoding a polypeptide having β-glucosidase activity;

(c) a polynucleotide consisting of a nucleotide sequence having at least 60% sequence identity with the nucleotide sequence represented by SEQ ID NO: 2 and encoding a polypeptide having β-glucosidase activity; and (d) a polynucleotide encoding the polypeptide according to [1].

[3] A polynucleotide that is any one of the following (a) to (d):

(a) a polynucleotide consisting of a nucleotide sequence represented by SEQ ID NO: 2;

(b) a polynucleotide consisting of a nucleotide sequence obtained by substituting, deleting, inserting and/or adding one or several nucleotides in the nucleotide sequence represented by SEQ ID NO: 2 and encoding a polypeptide having β-glucosidase activity;

(c) a polynucleotide consisting of a nucleotide sequence having at least 50% sequence identity with the nucleotide sequence represented by SEQ ID NO: 2 and encoding a polypeptide having β-glucosidase activity; and (d) a polynucleotide encoding the polypeptide according to [1].

[4] An expression vector comprising the polynucleotide according to [2] or [3].

[5] A transformant comprising the polynucleotide according to [2] or [3], or the expression vector according to [4].

[6] A transformed filamentous fungus of the genus *Trichoderma* comprising the polynucleotide according to [2] or [3], or the expression vector according to [4].

[7] A method for producing an enzyme composition comprising the step of culturing the transformant according to [5] or the transformed filamentous fungus of the genus *Trichoderma* according to [6].

[8] A method for producing a sugar solution from a cellulose-containing biomass, comprising the step of producing the enzyme composition according to [7], wherein the enzyme composition obtained by the step is used to produce the sugar solution.

[9] A β-glucosidase derived from a protist of the genus *Pseudotrichonympha*, wherein an activity of the β-glucosidase is 0.5 or more under a condition of a glucose concentration of 8 g/L when a β-glucosidase activity in the absence of glucose is taken as unity.

[10] An enzyme composition comprising a β-glucosidase derived from a protist of the genus *Pseudotrichonympha* and a cellulase derived from a filamentous fungus.

[11] The enzyme composition according to [10], wherein the filamentous fungus is a filamentous fungus of the genus *Trichoderma*.

[12] A method for producing a sugar solution from a cellulose-containing biomass using the enzyme composition according to [10] or [11].

[13] The method for producing a sugar solution according to [12], comprising the step of recovering the enzyme composition according to [10] or [11] from the sugar solution.

The specification incorporates the contents disclosed in JP Patent Application No. 2017-165787, based on which this application claims the priority.

Advantageous Effects of Invention

The present invention can provide a β-glucosidase having an effect of promoting saccharification efficiently in hydrolysis of cellulose-containing biomass. The β-glucosidase of the present invention can be suitably used for production of a sugar solution by hydrolysis of cellulose-containing biomass.

BRIEF DESCRIPTION OF DRAWINGS

FIG. 5 is a graph of measurement results on the inhibitory action of glucose on the β-glucosidase activity in the β-glucosidase of the present invention and the β-glucosidase mutant of the present invention in Example 18.

DESCRIPTION OF EMBODIMENTS

Figure 1:
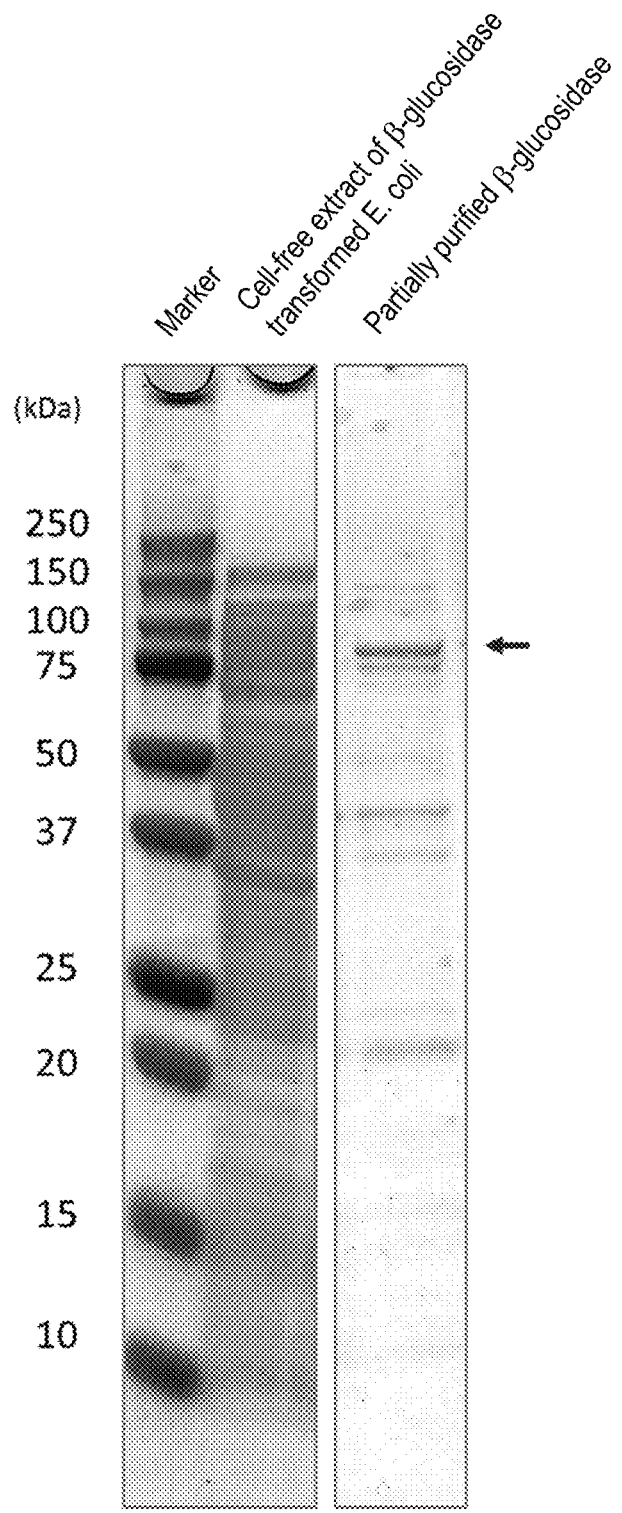
FIG. 1 is a photograph of SDS-PAGE of β-glucosidase β-glucosidase including the amino acid sequence represented by SEQ ID NO:1) according to the present invention, which was expressed in *E. coli* and purified in Example 7.

Hereafter, embodiments of the present invention will be described in details.

In the present invention, "β-glucosidase" means an enzyme that catalyzes a reaction for hydrolysis degradation of a sugar β-glucoside bond. In the present invention, a method for measuring a β-glucosidase activity utilizes a reaction using p-nitrophenyl-β-D-glucopyranoside (pNP-Glc) as a substrate. Specifically, an enzyme liquid is added to a substrate solution prepared by dissolving pNP-Glc in 50 mM acetic acid-sodium acetate buffer solution (pH 5.0) and reacted at 30° C. for 10 minutes; and the reaction is stopped by well mixing with 2M sodium carbonate in an amount equivalent to one-tenth of a reaction system volume to measure an increase of the absorbance at 405 nm. When p-nitrophenol is released and the absorbance at 405 nm is increased after the above reaction, it is determined that the β-glucosidase activity is present.

The β-glucosidase of the present invention is characterized by being derived from a protist of the genus *Pseudotrichonympha*, and specific examples thereof include a polypeptide consisting of an amino acid sequence represented by SEQ ID NO: 1 and a homolog thereof.

More specifically, the β-glucosidase derived from a protist of the genus *Pseudotrichonympha* of the present invention is any one of polypeptides of the following (A) to (C).

(A) a polypeptide consisting of an amino acid sequence represented by SEQ ID NO: 1;

(B) a polypeptide consisting of an amino acid sequence obtained by substituting, deleting, inserting and/or adding one or several amino acids in the amino acid sequence represented by SEQ ID NO: 1 and having β-glucosidase activity; and (C) a polypeptide consisting of an amino acid sequence having at least 70% sequence identity with the amino acid sequence represented by SEQ ID NO: 1 and having β-glucosidase activity.

As long as a polypeptide consisting of an amino acid sequence represented by SEQ ID NO: 1 or a homolog thereof can be prepared by a known method and the polypeptide has β-glucosidase activity, the method for preparing it is not particularly limited. The polypeptide consisting of an amino acid sequence represented by SEQ ID NO: 1 or a homolog thereof can be extracted from a natural product by a known method or prepared by a known method as a peptide synthesis method; or can be prepared by genetic recombination technology using a polynucleotide encoding an amino acid sequence of the polypeptide.

As long as the homolog of the polypeptide consisting of an amino acid sequence represented by SEQ ID NO: 1 is a polypeptide having β-glucosidase activity, it may be, for example, a polypeptide consisting of an amino acid sequence obtained by substituting, deleting, inserting and/or adding one or several amino acids, preferably 1 to 10 amino acids, more preferably 1 to 5 amino acids, and further preferably 1 or 2 amino acids in the amino acid sequence represented by SEQ ID NO: 1.

In addition, as long as the homolog of the polypeptide represented by SEQ ID NO: 1 is a polypeptide having β-glucosidase activity, it may be a polypeptide consisting of an amino acid sequence having at least 70%, preferably at least 80%, more preferably at least 90%, at least 95%, at least 97%, or at least 99% sequence identity with the amino acid sequence represented by SEQ ID NO: 1. Examples of a polypeptide consisting of an amino acid sequence having 88% sequence identity with SEQ ID NO: 1 include a polypeptide represented by SEQ ID NO: 6. In addition, examples of a polypeptide consisting of an amino acid sequence having 80% sequence identity with SEQ ID NO: 1 include a polypeptide represented by SEQ ID NO: 8. Note that regarding the sequence identity between the amino acid sequence represented by SEQ ID NO: 1 and the amino acid sequence of a known β-glucosidase, for example, β-glucosidase I (BGL I) derived from *Trichoderma reesei* consists of 744 amino acids, while its sequence identity with SEQ ID NO: 1 is 29%.

As long as the homolog of the polypeptide consisting of an amino acid sequence represented by SEQ ID NO: 1 is a polypeptide having β-glucosidase activity, it may be a polypeptide derived from a protist of the genus *Pseudotrichonympha*, preferably *Pseudotrichonympha hertwigi*, *Pseudotrichonympha paulistana*, or *Pseudotrichonympha grassii* of the genus *Pseudotrichonympha*.

β-glucosidase derived from a protist of the genus *Pseudotrichonympha* of the present invention preferably belongs to a GH3 family. In the present invention, "GH3 family" means a polypeptide including Glycosyl hydrolases family 3 active site. Glycosyl hydrolases family 3 active site is defined by the following amino acid sequence consisting of 18 amino acids. That is, Glycosyl hydrolases family 3 active site is defined by a sequence of 18 amino acids: aabxcxxxxGdefgDxxh consisting of the following amino acids a, b, c, d, e, f, g, h and x, and amino acids G (glycine) and D (aspartic acid), wherein a represents one amino acid selected from any of L (leucine), I (isoleucine), V (valine) and M (methionine); b represents one amino acid selected from any of amino acids K (lysine) and R (arginine); c represents one amino acid selected from any of amino acids E (glutamic acid), Q (glutamine), K (lysine), R (arginine) and D (aspartic acid); d represents one amino acid selected from any of amino acids L (leucine), I (isoleucine), V (valine), M (methionine), F (phenylalanine), T (threonine) and C (cysteine); e represents one amino acid selected from any of amino acids L (leucine), I (isoleucine), V (valine) and T (threonine); f represents one amino acid selected from any of amino acids L (leucine), I (isoleucine), V (valine), M (methionine) and F (phenylalanine); g represents one amino acid selected from any of amino acids S (serine) and T (threonine); h represents one amino acid selected from any of amino acids S (serine), G (glycine), A (alanine), D (aspartic acid), N (asparagine), I (isoleucine) and T (threonine); and x represents any amino acid. Note that Glycosyl hydrolases family 3 active site in a polypeptide can be easily investigated by anyone at the web site PROSITE (Database of protein domains, families and functional sites) (http://prosite.expasy.org/) as a database (Christian, et al. 2002, Briefings in Bioinfomatics, Vol. 3, No. 3, pages 265 to 274). The polypeptide consisting of an amino acid sequence represented by SEQ ID NO: 1, 6 or 8 belongs to GH 3 family.

The β-glucosidase derived from a protist of the genus *Pseudotrichonympha* of the present invention is preferably less likely to suffer from inhibition by glucose on the β-glucosidase activity. Specifically, when the β-glucosidase activity in the absence of glucose is taken unity, the β-glucosidase activity under a condition of a glucose concentration of 8 g/L (or in the presence of 8 g/L glucose) is preferably 0.5 or more, more preferably 0.6 or more, more preferably 0.7 or more, more preferably 0.8 or more, more preferably 0.9 or more, more preferably 1.0 or more, more preferably 1.1 or more, more preferably 1.2 or more, more preferably 1.3 or more, and in particular preferably 1.4 or more. Further, in addition to the β-glucosidase activity under the condition of the glucose concentration of 8 g/L, when the β-glucosidase activity in the absence of glucose is taken as unity, the β-glucosidase activity under a condition of a glucose concentration of 20 g/L (or in the presence of 20 g/L glucose) is preferably 0.5 or more, more preferably 0.6 or more, and in particular preferably 0.7 or more. The method used herein for measuring the β-glucosidase activity is the same as the above-described method except that 8 g/L or 20 g/L of glucose is added at the time of measuring; and results obtained thereby are used.

β-glucosidase, which is less likely to suffer from inhibition on the β-glucosidase activity by glucose, is preferred since it can maintain a high β-glucosidase activity even when glucose is produced in a saccharified reaction solution by cellulose degradation in the saccharification of cellulose-containing biomass.

As long as the polynucleotide consisting of a nucleotide sequence represented by SEQ ID NO:2 or a homolog thereof is a polynucleotide encoding a polypeptide consisting of the amino acid sequence represented by SEQ ID NO: 1 or the homolog thereof, its origin is not particularly limited. "Polynucleotide" used herein is preferably DNA though it is originated from whatever such as cDNA, genome DNA, synthetic DNA, mRNA, synthetic RNA or replicon RNA. In addition, it may be a single-stranded chain, or a double-stranded chain having a complementary chain thereof. In addition, it may include a naturally-occurring or artificial nucleotide derivative.

As long as the homolog of the polynucleotide represented by SEQ ID NO: 2 is a polynucleotide encoding a polypeptide having β-glucosidase activity, it may be, for example, a polynucleotide consisting of a nucleotide sequence obtained by substituting, deleting, inserting and/or adding one or several nucleotides, preferably 1 to 40 nucleotides, more preferably 1 to 30 nucleotides, further preferably 1 to 20 nucleotides, in particular preferably 1 to 10 nucleotides, and optimally preferably 1 to 5 nucleotides in the nucleotide sequence represented by SEQ ID NO: 2.

In addition, as long as the homolog of the polynucleotide represented by SEQ ID NO: 2 is polynucleotide encoding a polypeptide having β-glucosidase activity, it may be a polynucleotide hybridizable, under a stringent condition, with the entire or a part of the polynucleotide consisting of the nucleotide sequence represented by SEQ ID NO: 2 or a complementary chain thereof "Polynucleotide hybridizable under a stringent condition" used herein is a polynucleotide, which is hybridizable using as a probe, for example, one or more polynucleotides selected from at least any of 20, preferably at least 25, more preferably at least 30 continuous sequences of the original nucleotide sequence using a known hybridization technology (Current Protocols I Molecular Biology edit. Ausubel et al., (1987) Publish. John Wily & Sons Section, 6.3-6.4). The stringent condition mentioned herein can be implemented by washing using 0.1 to 2 times concentrated SSC (saline-sodium citrate) solution (1-fold concentration of composition of SSC solution: 150 mM sodium chloride and 15 mM sodium citrate), for example, in the presence of 50% formamide at a hybridization temperature of 37° C., 42° C. as a stricter condition, and 65° C. as a further stricter condition.

In addition, as long as the homolog of the polynucleotide represented by SEQ ID NO: 2 is a polynucleotide encoding a polypeptide having β-glucosidase activity, it may be a polynucleotide consisting of a nucleotide sequence having at least 50%, preferably at least 60%, more preferably at least 80%, further preferably at least 90%, at least 95%, at least 97% or at least 99% sequence identity relative to the nucleotide sequence represented by SEQ ID NO: 2. Examples of a polynucleotide consisting of a nucleotide sequence with 66% sequence identity with SEQ ID NO: 2 include a polynucleotide represented by SEQ ID NO: 3. In addition, examples of a polynucleotide consisting of a nucleotide sequence with 53% sequence identity with SEQ ID NO: 2 include a polynucleotide represented by SEQ ID NO: 7 or 9.

The term "identity" used in the present specification represents an agreement degree among two different amino acid sequences or nucleotide sequences when they are subjected to alignment comparison using a sequence alignment program, which is specifically a ratio (%) of the number of identical amino acids relative to the total number of amino acids of SEQ ID NO: 1 or a ratio (%) of the number of identical nucleotides relative to the total number of nucleotides of SEQ ID NO: 2. As the sequence alignment program used for alignment comparison of two sequences, BLAST (blastn, blastp), which is a software generally used in this field, is utilized. BLAST is available to anyone through a website of NCBI (National Center for Biotechnology Information), and the identity can be easily investigated by using parameters as defaults.

As long as the homolog of the polynucleotide consisting of the nucleotide sequence represented by SEQ ID NO: 2 is a polynucleotide encoding a polypeptide having β-glucosidase activity, it may be a polypeptide derived from a protist of the genus *Pseudotrichonympha*, preferably *Pseudotrichonympha hertwigi*, *Pseudotrichonympha paulistana*, or *Pseudotrichonympha grassii* of the genus *Pseudotrichonympha*.

The polynucleotide consisting of a nucleotide sequence represented by SEQ ID NO: 2 can be prepared by cloning from a protist of the genus *Pseudotrichonympha*, or it can be chemically synthesized. The cloning from a protist of the genus *Pseudotrichonympha* enables isolation through use of a generally known method, and for example, using a method including determining the entire ORF sequence from cDNA reverse-transcribed from RNA isolated from protist cells of the genus *Pseudotrichonympha* and then amplifying it by PCR, or it can be chemically synthesized directly by a DNA synthesis device.

The polynucleotide is ligated to the downstream of a promoter that can be expressed in a host cell by using a restriction enzyme and a DNA ligase, and thereby, an expression vector including the polynucleotide can be produced. In the present invention, as long as the expression vector is a vector that introduces a target gene in a host cell in an expressible manner, it may be any vector. It may be a plasmid that is autonomously replicable in such a form that the target gene is introduced outside the host genome while it may be a DNA fragment in such a form that the target gene can be introduced inside the host genome. Examples of the expression vector include a bacterial plasmid, a yeast plasmid, a phage DNA such as lambda phage, a virus DNA such as a retrovirus, a baculovirus, a vaccinia virus and an adenovirus, and *Agrobacterium* as a vector. For example, when a host cell is *Escherichia coli*, examples thereof include pUC, pET and pBAD. As long as the promoter is a suitable promoter corresponding to a host cell used for the expression of a gene, it may be any promoter. For example, when the host cell is *Escherichia coli*, examples thereof include lac promoter, a Trp promoter, a PL promoter and a PR promoter. When the host cell is a celullase-producible filamentous fungus, it is preferably a cellulose-inducible promoter, and more preferred examples thereof include a cbh promoter, an egl promoter, a bgl promoter, an xyn promoter and a bxl promoter.

As the host cell for a transformant having the polynucleotide or expression vector of the present invention, preferred are *Escherichia coli*, a bacterial cell, a yeast cell, a fungal cell, an insect cell, a plant cell, and an animal cell. Examples of the yeast cell include the genus *Pichia*, the genus *Saccharomyces*, and the genus *Schizosaccharomyces*. Examples of the insect cell include Sf9; examples of the plant cell include a dicotyledonous plant cell; and examples of the animal cell include CHO, HeLa, and HEK293. Exemplified are further preferably a fungal cell of a filamentous fungus, more preferably a filamentous fungus of the genus *Aspergillus*, and more preferably a filamentous fungus of the genus *Trichoderma*. Use of a filamentous fungus of the genus *Trichoderma* as the host cell can produce β-glucosidase of the present invention much more.

Transformation or transfection can be carried out by a known method such as calcium phosphate method, electroporation method, and *Agrobacterium* method.

The β-glucosidase of the present invention can be obtained by expressing it in a transformed or transfected host cell as described above under the control of the promoter and collecting a resultant product. For the expression, host cells are proliferated or grown up to a suitable cell density; then, the promoter is induced by a temperature shift or chemically inducing means with a medium component; and the cells are cultured further for a certain period.

In the present invention, an enzyme composition indicates a mixture of β-glucosidase derived from a protist of the genus *Pseudotrichonympha* and one or more other enzymes. The enzyme composition may be prepared by producing the β-glucosidase and the one or more other enzymes separately and then mixing them; and it may be a culture of a transformant having a polynucleotide or an expression vector encoding the polypeptide having β-glucosidase activity, wherein the culture contains the β-glucosidase and the one or more enzymes derived from host cells. The culture includes, in addition to a culture supernatant, a transformant or a homogenate of the transformant.

As the enzyme to be mixed with the β-glucosidase, preferred is cellulase. As long as cellulase mentioned herein is an enzyme having an activity to degrade cellulose, it is not particularly limited and it may be a mixture of two or more enzymes. Examples of such an enzyme include cellulase, hemicellulase, cellobiohydrolase, endoglucanase, exoglucanase, xylanase and mannanase. The activity of cellobiohydrolase and endoglucanase included in cellulase is measured by using p-nitrophenyl-β-D-lactopyranoside (pNP-Lac) as a substrate; and the activity of β-xylosidase is measured by using p-nitrophenyl-β-D-xylopyranoside (pNP-Xyl) as a substrate. Specifically, an enzyme liquid is added to a substrate solution prepared by dissolving pNP-Lac in 50 mM acetic acid-sodium acetate buffer solution (pH 5.0) and reacted at 30° C. for 10 minutes; and the reaction is stopped by well mixing with 2M sodium carbonate in an amount equivalent to one-tenth of a reaction system volume to measure an increase of the absorbance at 405 nm. If p-nitrophenol is released and the absorbance at 405 nm is increased after the above reaction, it is determined that the cellobiohydrolase activity and the endoglucanase activity are present. Regarding the β-xylosidase activity, the same reaction as above by using pNP-Xyl as a substrate is carried out. If p-nitrophenol is released and the absorbance at 405 nm is increased after the above reaction, it is determined that β-xylosidase activity is present.

The cellulase is preferably cellulase derived from a filamentous fungus. The cellulase derived from a filamentous fungus is a mixture containing at least both of endoglucanase and cellobiohydrolase. Examples of microorganisms capable of producing the filamentous fungus-derived cellulase include microorganisms of the genus *Trichoderma*, the genus *Aspergillus*, the genus *Cellulomonas*, the genus *Clostridium*, the genus *Streptomyces*, the genus *Humicola*, the genus *Acremonium*, the genus *Irpex*, the genus *Mucor* and the genus *Talaromyces*. These microorganisms produce cellulase in a culture solution, and thus, that culture solution may be used directly as unpurified filamentous fungus-derived cellulase. Alternatively, the culture solution is purified and formulated, which may be used as a filamentous fungus-derived cellulase mixture.

The filamentous fungus-derived cellulase is preferably cellulase derived from the genus *Trichoderma*. The genus *Trichoderma* produces cellulase containing at least two kinds of endoglucanases and at least two kinds of cellobiohydrolases in a culture solution, and cellulase prepared from such a culture solution can be preferably used for the present invention. That is, when the β-glucosidase of the present invention is used as an enzyme composition together with cellulase derived from the genus *Trichoderma*, this can increase a sugar yield in the saccharification of cellulose-containing biomass.

When cellulose-containing biomass is enzymatically treated with β-glucosidase of the present invention, the β-glucosidase of the present invention having a high remaining activity can be recovered from a saccharified solution obtained by enzymatic treatment. In addition, β-glucosidase of the present invention having a high remaining activity can be recovered from a saccharified solution obtained by enzymatically treating cellulose-containing biomass with the enzyme composition containing the β-glucosidase of the present invention and the filamentous fungus-derived cellulase. Further, regarding a filamentous fungus-derived enzyme composition, filamentous fungus-derived cellulase having a high remaining activity can be recovered from a saccharified solution obtained by enzymatically treating cellulose-containing biomass with the enzyme composition containing the β-glucosidase of the present invention and the filamentous fungus-derived cellulase in comparison with a saccharified solution obtained by enzymatically treating cellulose-containing biomass with only filamentous fungus-derived cellulase. As the filamentous fungus-derived cellulase, endoglucanase, cellobiohydrolase, β-xylosidase and others derived from the genus *Trichoderma* are preferred, and in particular, β-xylosidase is preferred.

More preferred are cellulases derived from *Trichoderma reesei* among the above genus *Trichoderma*. Examples of a cellulase mixture derived from *Trichoderma reesei* include cellulase mixtures derived from *Trichoderma reesei* QM9414, *Trichoderma reesei* QM9123, *Trichoderma reesei* Rut-30, *Trichoderma reesei* PC3-7, *Trichoderma reesei* CL-847, *Trichoderma reesei* MCG77, *Trichoderma reesei* MCG80 and *Trichoderma viride* QM9123. In addition, the cellulase mixture may be a cellulase mixture derived from cellulase productivity-improved mutants derived from the above genus *Trichoderma*, which have been mutated by a mutagen or ultraviolet irradiation.

In the present invention, as long as a method for producing an enzyme composition including a step of culturing a transformant having a polynucleotide or an expression vector introduced therein wherein they encode a polypeptide having the β-glucosidase activity, is a method including a culturing step capable of expressing the β-glucosidase, it may be any method. When the transformant is cultured, the expression of polypeptide having β-glucosidase activity is newly added or increased in the transformant, and as a result, an enzyme composition including the β-glucosidase and one or more host cell-derived enzymes is obtained from the culture. The culture may be, in addition to a culture supernatant, a transformant and a homogenate of the transformant.

The method for culturing the transformant is not particularly limited, and a known method is adopted. For culturing, various culture methods can be adopted, such as shaking culture, agitation culture, agitation and shaking culture, standing culture, and continuous culture. As a medium for culturing the transformant, any of natural media and synthetic media can be used as long as it is a medium that contains a carbon source, a nitrogen source, inorganic salts and others assimilable by the transformant and in which the transformant is efficiently cultured. When the transformant is a filamentous fungus of the genus *Trichoderma*, it is preferred to culture in a medium containing cellulose-containing biomass. Cellulase derived from a filamentous fungus of the genus *Trichoderma* is expressed by culturing a transformed filamentous fungus of the genus *Trichoderma* having a polynucleotide or expression vector encoding β-glucosidase of the present invention introduced therein in a medium containing cellulose-containing biomass, thereby enabling the production of an enzyme composition containing cellulase derived from the filamentous fungus of the genus *Trichoderma* and the β-glucosidase.

In the present invention, the cellulose-containing biomass is not limited as long as it contains at least cellulose. Specifically, examples thereof include bagasse, cone stover, corncob, switchgrass, rice straws, wheat straws, trees, wood materials, waste building materials, newspaper, waster paper, and pulp. These kinds of cellulose-containing biomass contain impurities such as a high molecule aromatic compound lignin or hemicellulose; however, they can be also used as cellulose-containing biomass when lignin or hemicellulose is completely or partially degraded or removed as a pre-treatment using acid, alkali, pressurized hot water or the like.

The method for producing a sugar solution from cellulose-containing biomass using the enzyme composition is not particularly limited. Production of a sugar solution using the enzyme composition may be carried out in a batch mode or continuous mode. In addition, the used enzyme composition can be separated and recovered from a saccharified solution obtained by enzymatic treatment of cellulose-containing biomass. A method for separating and recovering an enzyme is not particularly limited; however, the saccharified solution is filtrated by an ultrafilter membrane or the like and collection is implemented at a non-permeation side. Solids may be removed from the saccharified solution as a pretreatment of filtration if necessary. The recovered enzyme composition can be used again for saccharification reaction.

EXAMPLES (Reference Example 1) Method for Measuring the Concentration of Protein A commercially-available protein concentration measurement reagent (Quick Start Bradford protein assay, manufactured by Bio-Rad) was used. To 250 μL of protein concentration measurement reagent that had been brought back to room temperature, 5 μL of diluted filamentous fungus-derived cellulase solution was added. The mixture was left to stand at room temperature for 5 minutes, and thereafter, an absorbance thereof at 595 nm was measured using a microplate reader. BSA was used as a standard preparation and the protein concentration was calculated by referring to a calibration curve.

(Reference Example 2) Method for Measuring β-Glucosidase Activity

10 μL of an enzyme diluted solution was added to and reacted with 90 μL of 50 mM acetic acid buffer containing 1 mM p-nitrophenyl-β-glucopyranoside (manufactured by Sigma-Aldrich Japan) at 30° C. for 10 minutes. Thereafter, 10 μL of 2M sodium carbonate was added and well mixed to stop the reaction, and an increase of absorbance at 405 nm was measured. The activity to release 1 μmol of p-nitrophenol per minute was defined as 1 U. For a blank, 10 μL of 2M sodium carbonate was added to and well mixed with 90 μL of 50 mM sodium acetate buffer containing 1 mM p-nitrophenyl-β-glucopyranoside, and thereafter, 10 μL of an enzyme diluted solution was added to cause a reaction at 30° C. for 30 minutes. Thereafter, an increase of absorbance at 405 nm was measured. At this time, the enzyme liquid was diluted so as not to exceed an absorbance at 405 nm of 1. In addition, a calibration curve was created based on absorbances measured by preparing p-nitrophenol solutions at concentrations of 0.1 mM, 0.2 mM, 1 mM and 2 mM; using 10 μL of them instead of an enzyme diluted solution; and adding and well mixing 10 μL of 2M sodium carbonate for color development.

(Reference Example 3) Method for Measuring β-Xylosidase Activity

10 μL of an enzyme diluted solution was added to and reacted with 90 μL of 50 mM acetic acid buffer containing 1 mM p-nitrophenyl-β-xylopyranoside (manufactured by Sigma-Aldrich Japan) at 30° C. for 30 minutes. Thereafter, 10 μL of 2M sodium carbonate was added and well mixed to stop the reaction, and an increase of absorbance at 405 nm was measured. The activity to release 1 μmol of p-nitrophenol per minute was defined as 1 U. For a blank, 10 μL of 2M sodium carbonate was added to and well mixed with 90 μL of 50 mM acetic acid buffer containing 1 mM p-nitrophenyl-β-xylopyranoside, and thereafter, 10 of an enzyme diluted solution was added to cause a reaction at 30° C. for 30 minutes. Thereafter, an increase of absorbance at 405 nm was measured. At this time, the enzyme liquid was diluted so as not to exceed an absorbance at 405 nm of 1. In addition, a calibration curve was created based on absorbances measured by preparing p-nitrophenol solutions at concentrations of 0.1 mM, 0.2 mM, 1 mM and 2 mM; using 10 μL of them instead of an enzyme diluted solution; and adding and well mixing 10 μL of 2M sodium carbonate for color development.

(Reference Example 4) Method for Measuring Cellobiohydrolase/Endoglucanase Activity 10 μL of an enzyme diluted solution was added to and reacted with 90 μL of 50 mM acetic acid buffer containing 1 mM p-nitrophenyl-β-lactopyranoside (manufactured by Sigma-Aldrich Japan) at 30° C. for 60 minutes. Thereafter, 10 μL of 2M sodium carbonate was added and well mixed to stop the reaction, and an increase of absorbance at 405 nm was measured. The activity to release 1 μmol of p-nitrophenol per minute was defined as 1 U. For a blank, 10 μL of 2M sodium carbonate was added to and well mixed with 90 μL of 50 mM acetic acid buffer containing 1 mM p-nitrophenyl-β-lactopyranoside, and thereafter, 10 μL of an enzyme diluted solution was added to cause a reaction at 30° C. for 30 minutes. Thereafter, an increase of absorbance at 405 nm was measured. At this time, the enzyme liquid was diluted so as not to exceed an absorbance at 405 nm of 1. In addition, a calibration curve was created based on absorbances measured by preparing p-nitrophenol solutions at concentrations of 0.1 mM, 0.2 mM, 1 mM and 2 mM; using 10 μL of them instead of an enzyme diluted solution; and adding and well mixing 10 μL of 2M sodium carbonate for color development.

(Reference Example 5) Measurement of Sugar Concentration

Glucose and cellobiose were quantitatively analyzed using an ACQUITY UPLC system (Waters) under the following conditions.

Quantitative analysis was made by referring to a calibration curve created by authentic preparations of glucose and cellobiose. When the concentration of cellobiose was lower than 1 g/L, it was determined as a detection limit or lower.
Column: AQUITY UPLC BEH Amide 1.7 μm 2.1×100 mm Column
Separation method: HILIC
Mobile phase: an aqueous solution of 80% acetonitrile and 0.2% TEA (triethylamine) was used as mobile phase A and an aqueous solution of 30% acetonitrile and 0.2% TEA (triethylamine) was used as mobile phase B. The below-described gradient was adopted. The gradient was linear so as to reach mixing ratios corresponding to the following times.
Starting condition: (A: 99.90%, B: 0.10%), 2 minutes after starting (A: 96.70%, B: 3.30%), 3.5 minutes after starting (A: 95.00%, B: 5.00%), 3.55 minutes after starting (A: 99.90%, B: 0.10%), 6 minutes after starting (A: 99.90%, B: 0.10%)
Detection method: ELSD (Evaporation Light Scattering Detector)
Flow rate: 0.3 mL/min
Temperature: 55° C.

(Reference Example 6) SDS-PAGE

For SDS-PAGE, 15% polyacrylamide gel, e-PAGEL (Atto Corporation) was used. 5 μg of the enzyme from the β-glucosidase transformed *Trichoderma* strain was mixed with an equal volume of a sample buffer, Ez-apply (Atto Corporation) and heated at 95° C. for 10 minutes; and the result was used as an electrophoresis sample. As a molecular weight marker, Precision Plus Protein Dual Color Standards (BioRad) was used. An aqueous solution (25 mM Tris, 192 mM glycine, 0.1% SDS) was used as an electrophoresis buffer, and electrophoresis was conducted at a constant current of 20 mA for 90 minutes. The gel after electrophoresis was stained with Bio-Safe Comassie G-250 Stain (BioRad) and decolored with pure water.

(Reference Example 7) Cellulase Production by Culturing Filamentous Fungi of the Genus *Trichoderma*

Spores of filamentous fungi of the genus *Trichoderma* were diluted with a physiological saline solution so as to have a spore concentration of $1.0 \times 10^7$/mL. 2.5 mL of the diluted spore solution was inoculated into 250 mL of a culture solution having a composition described in Table 1 in a 1 L baffled flask; and cultured (precultured) for 3 days under culture conditions of 28° C. and 160 rpm. For a main culture, 250 mL of the preculture solution was each inoculated into 2.5 L of a main culture solution indicated in Table 2 in a 5 L mini jar; and cultured for 4 days under culture conditions of 28° C., 700 rpm, 1 vvm and pH 5. For neutralization, 10% ammonia and 1N sulfuric acid were used. The culture solution from 4 days later from the start of culture was centrifuged; a supernatant was filtrated by an ultrafilter membrane for removal of fungus bodies; and thereby, cellulase derived from filamentous fungi of the genus *Trichoderma* was obtained.

TABLE 1

| Component | Per 1 L |
| --- | --- |
| D-glucose | 20 g |
| 5× Mandel's** | 200 mL |
| 10× ammonium tartrate | 100 mL |
| Corn steep liquor | 15 g |
| Trace element* | 1 mL |
| Tween 80 | 0.5 mL |
| Antifoaming agent (PE-M) | 1 mL |

*Trace element solution contains 0.3 g/L $H_3BO_3$, 1.3 g/L $(NH_4)_6Mo_7O_{24} \times 4H_2O$, 5 g/L $FeCl_3 \times 6H_2O$, 2 g/L $CuSO_4 \times 5H_2O$, 0.4 g/L $MnCl_2 \times 4H_2O$ and 10 g/L $ZnCl_2$.
**Mandel's contains 7 g/L $(NH_4)_2SO_4$, 10 g/L $KH_2PO_4$, 3 g/L $CaCl_2$ and 3 g/L $MgSO_4 \times 7H_2O$.

TABLE 2

| Component | Per 1 L |
| --- | --- |
| Biomass *** | 100 g |
| 5× Mandel's** | 200 mL |
| Corn steep liquor | 25 g |

TABLE 2-continued

| Component | Per 1 L |
| --- | --- |
| Trace element* | 1 mL |
| Tween 80 | 0.5 mL |
| Antifoaming agent (PE-M) | 1 mL |

*Trace element solution contains 0.3 g/L $H_3BO_3$, 1.3 g/L $(NH_4)_6Mo_7O_{24} \times 4H_2O$, 5 g/L $FeCl_3 \times 6H_2O$, 2 g/L $CuSO_4 \times 5H_2O$, 0.4 g/L $MnCl_2 \times 4H_2O$ and 10 g/L $ZnCl_2$.
**Mandel's contains 7 g/L $(NH_4)_2SO_4$, 10 g/L $KH_2PO_4$, 3 g/L $CaCl_2$ and 3 g/L $MgSO_4 \times 7H_2O$.
*** Biomass used herein was Arbocel (registered trademark) (J. Rettenmaier & Sohne). Biomass was added after mixing of other components and diluting in the mini jar.

(Reference Example 8) Method for Measuring Inhibitory Action of Glucose on the β-Glucosidase Activity An enzyme solution was added to a mixture solution containing 1 mM p-nitrophenyl-β-glucopyranoside (manufactured by Sigma-Aldrich Japan), 50 mM acetic acid buffer and 0, 4, 8 or 20 g/L glucose such that the total amount of the reaction solution became 100 μL, causing a reaction at 30° C. for 100 minutes. Thereafter, 10 μL of 2M sodium carbonate was added and well mixed to stop the reaction, and an increase of absorbance at 405 nm was measured. The activity to release 1 μmol of p-nitrophenol per minute was defined as 1 U. For a blank, 10 μL of 2M sodium carbonate was added to an amount, equivalent to that of the above mixture solution for the reaction solution before addition of the enzyme solution, of a mixture solution containing 1 mM p-nitrophenyl-β-glucopyranoside, 50 mM sodium acetate buffer and 0, 4, 8 or 20 g/L glucose, and mixed well; and then, the enzyme solution was added such that the total solution amount of the blank became 110 μL, causing a reaction at 30° C. for 30 minutes. Thereafter, an increase of absorbance at 405 nm was measured.

(Example 1) RNA-Seq Analysis from a Hardly-Culturable Single Cell of Symbiont of *Coptotermes formosanus*, and Analysis of β-Glucosidase Candidate Sequence

*Pseudotrichonympha grassii* cells were selected from hardly-culturable symbiotic protist community of termites contained in extracts of the intestinal tract of *Coptotermes formosanus* and fractionated by a micro capillary; and RNA extraction from a single cell, reverse transcription, cDNA amplification, conversion to a library and sequencing were carried out by Quartz-seq method of Sasagawa, et al. (Sasagawa, Y., et al.: Genome Biol., 14: R31, 2013). From results of the sequencing, nucleotide sequences encoding β-glucosidase candidates were selected. A tool, SignalP (http:www.cbs.dtu.dk/services/SignalP/) capable of predicting a signal sequence of a protein was used to predict a signal sequence portion of an amino acid sequence as encoded by the nucleotide sequence. As a result, an amino acid sequence represented by SEQ ID NO: 1 as β-glucosidase candidate sequence excluding a signal sequence; and a nucleotide sequence of SEQ ID NO: 2 as a nucleotide sequence encoding the amino acid sequence were obtained. After a family of the amino acid sequence represented by SEQ ID NO: 1 was investigated by PROSITE, it has been found that positions 259 to 276 of SEQ ID NO: 1 have an amino acid sequence of SEQ ID NO: 5 corresponding to Glycosyl hydrolases family 3 active site.

(Example 2) Production of β-Glucosidase Gene Transformed *E. coli*

A plasmid wherein the polynucleotide represented by SEQ ID NO: 2 (nucleotide sequence encoding a β-glucosidase candidate gene derived from a protist of the genus *Pseudotrichonympha*), obtained in Example 1, was ligated to NdeI and XhoI restriction enzyme sites of pET14b, was synthesized by an artificial gene synthesis service (Genscript). The constitution of the plasmid sequence used herein was designed to express β-glucosidase having an amino acid sequence represented by SEQ ID NO: 1, having His-tag added to the N-terminal in the transformant. The plasmid was transformed into *E. coli* (Rossetta2 (DE3)) strain.

(Example 3) Production of Cell-Free Extract of β-Glucosidase Gene Transformed *E. coli*

β-glucosidase gene transformed *E. coli* produced in Example 2 were inoculated into 10 mL of an ampicillin-containing LB medium, and subjected to shaking culture (preculture) at 37° C. overnight. As a main culture, microbes obtained in the preculture were inoculated into an ampicillin-containing LB medium and subjected to shaking culture at 37° C. until the turbidity OD600 at a wavelength of 600 nm became 0.8. Thereafter, isopropyl-1-thio-β-D-galactoside (IPTG) was added such that the final concentration becomes 0.1 mM, and further overnight culture was carried out at 16° C. After the culture, the microbes were collected by centrifugation and resuspended in 50 mM Tris-HCl buffer (pH 7.6). This solution was ultrasonically homogenized while being ice-cold, and a supernatant thereof was collected as a cell-free extract by centrifugation. When the β-glucosidase activity was measured on the cell-free extract of the β-glucosidase candidate gene transformed *E. coli*, it was 0.14 U per 1 mg of protein contained in the cell-free extract. In addition, the entire β-glucosidase activity obtained from 1 L of the culture solution of the β-glucosidase gene transformed *E. coli* was 21.6 U. As a comparative control, a cell-free extract of transformant having a plasmid containing no β-glucosidase candidate gene was prepared in the same manner; and when the β-glucosidase activity was measured, it was not detected. That is, the β-glucosidase activity was detected only from the cell-free extract that has expressed a polypeptide wherein His-tag was added to the amino acid sequence represented by SEQ ID NO: 1. It was therefore found that the polypeptide consisting of the amino acid sequence represented by SEQ ID NO: 1 was a β-glucosidase sequence derived from a protist of the genus *Pseudotrichonympha*.

(Example 4) Production of β-Glucosidase Mutant Gene Transformed *E. coli*

Plasmids wherein each of polynucleotides represented by SEQ ID NOs: 7 and 9 having 53% sequence identity with SEQ ID NO: 2 was ligated to NdeI and XhoI restriction enzyme sites of pET14b were synthesized by an artificial gene synthesis service (Genscript) in the same manner as in Example 2. The constitutions of the plasmid sequence used herein were designed to express β-glucosidases having amino acid sequences represented by SEQ ID NOs: 6 and 8, respectively, having His-tag added to the N-terminal in the transformant. The plasmid was transformed into *E. coli* (Rossetta2 (DE3)) strain.

(Example 5) Production of Cell-Free Extract of β-Glucosidase Mutant Gene Transformed *E. coli*

β-glucosidase mutant gene transformed *E. coli* produced in Example 4 were inoculated into 10 mL of an ampicillin-containing LB medium, and subjected to shaking culture (preculture) at 37° C. overnight. As a main culture, microbes obtained in the preculture were inoculated into an ampicillin-containing LB medium and subjected to shaking culture at 37° C. until the turbidity OD600 at a wavelength of 600 nm became 0.8. Thereafter, isopropyl-1-thio-β-D-galactoside (IPTG) was added such that the final concentration becomes 0.1 mM, and further overnight culture was carried out at 16° C. After the culture, the microbes were collected by centrifugation and resuspended in 50 mM Tris-HCl buffer (pH 7.6). This solution was ultrasonically homogenated while being ice-cold, and a supernatant thereof was collected as a cell-free extract by centrifugation. Then, after the volume of the extract was reduced to one-twelfth by an ultrafilter membrane unit, whether the β-glucosidase activity was present or absent was investigated. As a comparative control, a cell-free extract of transformant having a plasmid containing no β-glucosidase candidate gene was prepared in the same manner; and when whether the β-glucosidase activity was present or absent was investigated, it was not detected. That is, the β-glucosidase activity was detected only from the cell-free extract that has expressed a polypeptide wherein His-tag was added to the amino acid sequence represented by SEQ ID NO: 6 having 88% sequence identity with SEQ ID NO: 1 or SEQ ID NO: 8 having 80% sequence identity with SEQ ID NO: 1. It was therefore found that the polypeptide consisting of each of the amino acid sequences represented by SEQ ID NOs: 6 and 8 had β-glucosidase activity. Results of β-glucosidase activity measurements are shown in Table 3.

TABLE 3

|  | Mutant 1 | Mutant 2 | Comparative control |
|---|---|---|---|
| Amino acid sequence of β-glucosidase | SEQ ID NO: 6 | SEQ ID NO: 8 | None (plasmid only) |
| Increase of absorbance (405 nm) | 0.307 | 0.365 | Detection limit or less (<0.075) |

(Example 6) Preparation of Enzyme Composition Containing: Cell-Free Extract of β-Glucosidase Gene Transformed *E. coli*; and Cellulase Derived from the Genus *Trichoderma* Filamentous Fungus, and Saccharification of Powdered Cellulose from Wood Material In accordance with Reference Example 7, *Trichoderma reesei* was cultured and cellulase derived from the genus *Trichoderma* filamentous fungus was produced. An enzyme composition was prepared by mixing the cell-free extract of β-glucosidase gene transformed *E. coli* produced in Example 3 with the genus *Trichoderma* filamentous fungus-derived cellulase, and used for saccharification reaction. The mixing for the enzyme composition was conducted such that, per 1 mL of saccharification reaction solution, a protein concentration of the genus *Trichoderma* filamentous fungus-derived cellulase was 0.2 g/L and a protein concentration of the cell-free extract of β-glucosidase gene transformed *E. coli* was 2.1 g/L. As biomass for saccharification, powdered cellulose from wood material, Arbocel (registered tradename) (J. Rettenmaier & Sohne) was used. Saccharification reaction was conducted as follows. 50 mg of the biomass was fed into a 2-mL tube; a sodium acetate buffer (pH 5.2) was added such that the final concentration became 50 mM; and pure water was added such that a solid content of powdered cellulose from wood material became 5% by weight at the time of starting the reaction. Further, the enzyme composition was added to the prepared solution, and a heat block rotator was used to start the reaction under a reaction condition of 35° C. A sample after 24-hour saccharification reaction was centrifuged under a condition of 10,000×g for 5 minutes to separate a supernatant; an amount, which was one-tenth of a volume of the supernatant, of 1N sodium hydroxide solution was added to stop the saccharification reaction. The supernatant was filtrated with a 0.22 μm-filter, and the thus-obtained filtrate was provided for sugar analysis in accordance with Reference Example 5. For a comparative control, a cell-free extract of *E. coli* wherein only a vector containing no β-glucosidase gene was transformed was used; according to the same manner as described above, it was mixed with the genus *Trichoderma* filamentous fungus-derived cellulase such that, per 1 mL of saccharification reaction solution, a protein concentration became 2.1 g/L; and saccharification reaction and sugar analysis of a saccharified supernatant were performed. Then, the enzyme composition containing the cell-free extract of the β-glucosidase gene transformed *E. coli* and the genus *Trichoderma* filamentous fungus-derived cellulase as used for saccharification reaction had a higher β-glucosidase activity by 2.6 times than the genus *Trichoderma* filamentous fungus-derived cellulase containing no cell-free extract of the β-glucosidase gene transformed *E. coli*. The result of the saccharification reaction shows that when the enzyme composition containing the cell-free extract of the β-glucosidase gene transformed *E. coli* and the genus *Trichoderma* filamentous fungus-derived cellulase was added, the accumulated amount of glucose was increased by about 2.7 times while the accumulated amount of cellobiose was decreased in comparison with the case where the genus *Trichoderma* filamentous fungus-derived cellulase not containing β-glucosidase of the present invention was added. Results on glucose/cellobiose obtained by sugar analysis are shown in Table 4.

TABLE 4

|  | Enzyme composition containing the cell-free extract of the β-glucosidase gene transformed *E. coli* and the genus *Trichoderma* filamentous fungus-derived cellulase | Genus *Trichoderma* filamentous fungus-derived cellulase (Comparative control) |
| --- | --- | --- |
| Glucose (g/L) | 14.58 | 5.34 |
| Cellobiose (g/L) | Detection limit or less | 4.76 |

(Example 7) Partial Purification with His-Tag of β-Glucosidase

The cell-free extract of the β-glucosidase gene transformed *E. coli*, whose enzymatic activity was confirmed in Example 3, was subjected to Hig-tag purification. His-tag purification was performed using HisBind Purification Kit (Merck Millipore) and in accordance with a batch method in the manual. In accordance with Reference Example 6, when a purified fraction was subjected to SDS-PAGE, the darkest band was detected at molecular weights from 75 kDa to 100 kDa in an elution fraction; purification on His-tagged β-glucosidase with a theoretical molecular weight of 83.9 kDa was confirmed. A photograph of SDS-PAGE gel is shown in FIG. 1. In accordance with the method in the manual, the buffer for the elution fraction was exchanged with 20 mM Tris-HCl (pH 7.6) using a gel filtration column PD-10 (GE Healthcare), and the resultant product was regarded as a partially purified β-glucosidase. When the partially purified β-glucosidase was measured in terms of the protein concentration and the β-glucosidase activity, the activity was 3.50 U per 1 mg of protein contained in the partially purified β-glucosidase.

(Example 8) Preparation of Enzyme Composition Containing the Partially Purified β-Glucosidase and the Genus *Trichoderma* Filamentous Fungus-Derived Cellulase, and Saccharification of Powdered Cellulose from Wood Material In accordance with Reference Example 7, *Trichoderma reesei* was cultured and cellulase derived from the genus *Trichoderma* filamentous fungus was produced. An enzyme composition was prepared by mixing the partially purified β-glucosidase produced in Example 7 with the genus *Trichoderma* filamentous fungus-derived cellulase, and used for saccharification reaction. The mixing for the enzyme composition was conducted such that, per 1 mL of saccharification reaction solution, a protein concentration of the genus *Trichoderma* filamentous fungus-derived cellulase was 0.2 g/L and a protein concentration of the partially purified β-glucosidase was 0.017 g/L. Saccharification reaction and sugar analysis of a saccharified supernatant were conducted in the same manner as in Example 6 except that the partially purified β-glucosidase was used for the enzyme composition. For a comparative control, only the genus *Trichoderma* filamentous fungus-derived cellulase was used and added such that, per 1 mL of saccharification reaction solution, a protein concentration was 2.1 g/L in the same manner as above; and saccharification reaction and sugar analysis of a saccharified supernatant were performed. Then, the enzyme composition containing the partially purified β-glucosidase and the genus *Trichoderma* filamentous fungus-derived cellulase as used for saccharification reaction had a higher β-glucosidase activity by 1.6 times than only the genus *Trichoderma* filamentous fungus-derived cellulase. The result of the saccharification reaction shows that when the enzyme composition prepared by mixing the partially purified β-glucosidase with the *Trichoderma* cellulase was added, the accumulated amount of glucose was increased by about 1.8 times while the accumulated amount of cellobiose was decreased in comparison with the case where only the genus *Trichoderma* filamentous fungus-derived cellulase was added. Results on glucose/cellobiose obtained by sugar analysis are shown in Table 5.

TABLE 5

|  | Enzyme composition containing the partially purified β-glucosidase and the genus *Trichoderma* filamentous fungus-derived cellulase | Genus *Trichoderma* filamentous fungus-derived cellulase (Comparative control) |
| --- | --- | --- |
| Glucose (g/L) | 10.68 | 5.96 |
| Cellobiose (g/L) | 2.31 | 3.54 |

(Example 9) Production of the Genus *Trichoderma* Filamentous Fungus Transformed with β-Glucosidase Gene A plasmid wherein a polynucleotide represented by SEQ ID NO: 3 having 66% sequence identity with the nucleotide sequence represented by SEQ ID NO: 2 (nucleotide sequence encoding a β-glucosidase gene derived from a protist of the genus *Pseudotrichonympha*) was ligated to NdeI and XhoI restriction enzyme sites of pET14b, was synthesized by an artificial gene synthesis service (Genscript). From the plasmid, a nucleotide sequence portion of SEQ ID NO: 3 was PCR-amplified and ligated to the downstream of an endoglucanase 1 promoter derived from *Trichoderma reesei* so as to be in-frame with a secretion signal sequence of β-glucosidase of *Aspergillus aculeatus*, and the sequence and a hygromycin resistant gene of transformant were cloned between T-DNA borders of pB1101 plasmid. The sequence between T-DNA borders of the produced plasmid is shown in SEQ ID NO: 4. In this connection, SEQ IE NO: 4 was designed such that the sequence was introduced into a genome of a host cell so as to express and secrete β-glucosidase having an amino acid sequence represented by SEQ ID NO: 1, encoded by the following nucleotide numbers 978 to 3161 (SEQ ID NO: 3). The constitutions of SEQ ID NO: 4 are shown below.

LB=left T-DNA border: nucleotide Nos. 1 to 26
Pegl1=endoglucanase 1 promoter derived from *Trichoderma reesei*: nucleotide Nos. 27 to 920
Sbgl=β-glucosidase secretion signal derived from *Aspergillus aculeatus*: nucleotide Nos. 921 to 977
bgl=β-glucosidase derived from a protist of the genus *Pseudotrichonympha*: nucleotide Nos. 978 to 3161 (SEQ ID NO: 3)
Tegl1=endoglucanase 1 terminator derived from *Trichoderma reesei*: nucleotide Nos. 3162 to 4019
PamdS=acetamidase promoter derived from *Aspergillus nidulans*: nucleotide Nos. 4020 to 5027
hygR=hygromycin B phosphotransferase from *Streptomyces hygroscopicus*: nucleotide Nos. 5028 to 6065
TamdS=acetamidase terminator from *Aspergillus nidulans*: nucleotide Nos. 6066 to 6786
RB=right T-DNA border: nucleotide Nos. 6787 to 6810

The produced plasmid was introduced into an *Agrobacterium tumefaciens* AGL1 strain; *Trichoderma reesei* was infected with the transformed *Agrobacterium*; and a β-glucosidase transformed *Trichoderma* strain was obtained. Transformation of *Trichoderma* with *Agrobacterium* was conducted based on the method of Marcel, et al. (Marcel, et al. 2006, Nat Biotechnol 16: 839-842), in which the transformed *Agrobacterium* cultured for 8 hours in an Induction medium (IM) liquid medium containing glucose and acetosyringone was mixed with a spore solution of *Trichoderma reesei*, and cultured on a cellophane placed on an Induction medium (IM) solid medium for 3 days; the cellophane was moved onto a potato dextrose agar plate (selective medium) containing cefotaxime and hygromycin; purification culture including picking up colonies grown on the selective medium and sowing on the selective medium again was repeated twice; and a transformed *Trichoderma* strain was obtained.

(Example 10) Production of Enzyme Composition by Culturing β-Glucosidase Gene Transformed Filamentous Fungus of the Genus *Trichoderma*

Figure 2:
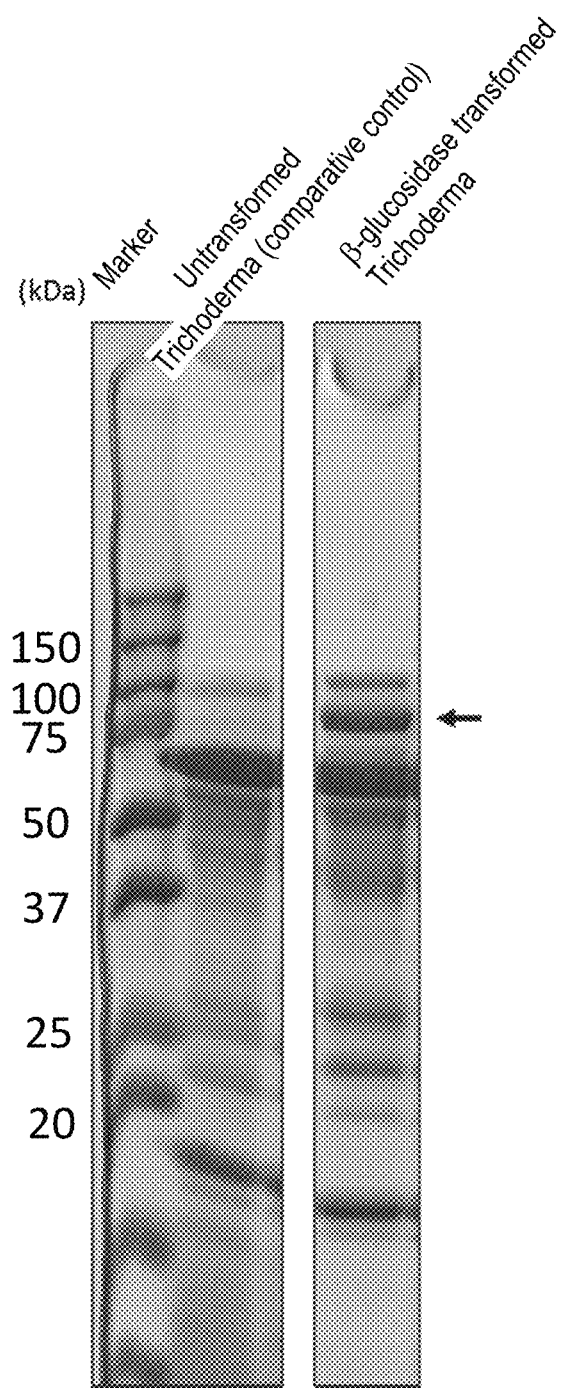
FIG. 2 is a photograph of SDS-PAGE of β-glucosidase β-glucosidase including an amino acid sequence represented by SEQ ID NO: 1) according to the present invention, which was expressed in the genus *Trichoderma* filamentous fungus in Example 10.

The β-glucosidase gene transformed filamentous fungus of the genus *Trichoderma* produced in Example 9 was cultured by the same method as in Reference Example 7. The culture solution after 4 days from the start of culture was centrifuged; a supernatant was filtrated by an ultrafilter membrane to remove fungal bodies; and thereby, an enzyme composition containing the β-glucosidase of the present invention expressed in filamentous fungus of the genus *Trichoderma* and the genus *Trichoderma* filamentous fungus-derived cellulase was prepared. The protein concentration of the enzyme composition was measured in accordance with Reference Example 1, and SDS-PAGE was conducted in accordance with Reference Example 6, so that the expressed protein was confirmed. For a comparative control, only the genus *Trichoderma* filamentous fungus-derived cellulase obtained by culturing untransformed genus *Trichoderma* filamentous fungi was used, and culture, collection of a supernatant, filtration of a cultured supernatant and SDS-PAGE were carried out in the same manner. As a result of SDS-PAGE, regarding the enzyme composition containing the β-glucosidase and the genus *Trichoderma* filamentous fungus-derived cellulase, the band of the β-glucosidase of the present invention was observed as a band larger than one-tenth of the total of the band of the enzyme composition confirmed by SDS-PAGE; and regarding the β-glucosidase gene transformed filamentous fungus of the genus *Trichoderma*, it was confirmed that large quantity of β-glucosidase of the present invention was expressed. A photograph of SDS-PAGE gel is shown in FIG. 2.

Further, in accordance with Reference Example 2, the enzyme composition containing the β-glucosidase and the genus *Trichoderma* filamentous fungus-derived cellulase was measured in terms of the β-glucosidase activity. As a result, the enzyme composition containing the β-glucosidase and the genus *Trichoderma* filamentous fungus-derived cellulase had a higher β-glucosidase activity by 2.0 times than the genus *Trichoderma* filamentous fungus-derived cellulase alone. In addition, the entire β-glucosidase activity obtained from 1 L of culture solution of the β-glucosidase gene transformed filamentous fungus of the genus *Trichoderma* was about $1.80 \times 10^3$ U, which provided, in terms of the β-glucosidase expression in the genus *Trichoderma* filamentous fungi, about 850 times of β-glucosidase compared to the β-glucosidase expression in *E. coli* in Example 3 from the same volume of culture solution. It was found that the productivity of the β-glucosidase of the present invention was high.

(Example 11) Saccharification of Microcrystal Cellulose by the Enzyme Composition Containing the β-Glucosidase and the Genus *Trichoderma* Filamentous Fungus-Derived Cellulase The enzyme composition containing the β-glucosidase and the genus *Trichoderma* filamentous fungus-derived cellulase prepared in Example 10 was used for saccharification reaction. As biomass for saccharification, microcrystal cellulose, Cellulose microcrystalline (manufactured by Merck) was used. Except the used biomass, saccharification reaction and sugar analysis of a saccharified supernatant were conducted in the same manner as in Example 6. An amount of enzyme added was 8 mg/g-biomass. For a comparative control, only the genus *Trichoderma* filamentous fungus-derived cellulase was used, and saccharification reaction and sugar analysis of a saccharified supernatant were performed in the same manner. As a result, the saccharification using the enzyme composition containing the β-glucosidase and the genus *Trichoderma* filamentous fungus-derived cellulase increased an accumulated amount of glucose by about 1.6 times and decreased an accumulated amount of cellobiose, compared to the saccharification using only the genus *Trichoderma* filamentous fungus-derived cellulase. Results on glucose/cellobiose obtained by sugar analysis are shown in Table 6.

TABLE 6

| Used enzyme | Enzyme composition containing β-glucosidase and the genus Trichoderma filamentous fungus-derived cellulase | Genus Trichoderma filamentous fungus-derived cellulase (Comparative control) |
|---|---|---|
| Glucose (g/L) | 20.96 | 12.80 |
| Cellobiose (g/L) | Detection limit or less | 3.19 |

(Example 12) Saccharification of Powdered Cellulose from Wood Material by the Enzyme Composition Containing the β-Glucosidase and the Genus *Trichoderma* Filamentous Fungus-Derived Cellulase The enzyme composition containing the β-glucosidase and the genus *Trichoderma* filamentous fungus-derived cellulase prepared in Example 10 was used for saccharification reaction. As biomass for saccharification, powdered cellulose from wood material, Arbocel (registered trademark) (J. Rettenmaier & Sohne) was used. Except for the used biomass, saccharification reaction and sugar analysis of a saccharified supernatant were conducted in the same manner as in Example 11. For a comparative control, only the genus *Trichoderma* filamentous fungus-derived cellulase was used, and saccharification and sugar analysis of a saccharified supernatant were conducted in the same manner. As a result, the saccharification using the enzyme composition containing the β-glucosidase and the genus *Trichoderma* filamentous fungus-derived cellulase increased an accumulated amount of glucose by about 1.8 times and gave no detectable accumulation of cellobiose, compared to the saccharification using only the genus *Trichoderma* filamentous fungus-derived cellulase. Results on glucose/cellobiose obtained by sugar analysis are shown in Table 7.

TABLE 7

| Used enzyme | Enzyme composition containing β-glucosidase and the genus Trichoderma filamentous fungus-derived cellulase | Genus Trichoderma filamentous fungus-derived cellulase (Comparative control) |
|---|---|---|
| Glucose (g/L) | 25.60 | 14.12 |
| Cellobiose (g/L) | Detection limit or less | 3.27 |

(Example 13) Saccharification of Alkali-Treated Bagasse by the Enzyme Composition Containing the β-Glucosidase and the Genus *Trichoderma* Filamentous Fungus-Derived Cellulase The enzyme composition containing the β-glucosidase and the genus *Trichoderma* filamentous fungus-derived cellulase prepared in Example 10 was used for saccharification reaction. As biomass for saccharification, alkali-treated (pretreated) bagasse was used. Except for the used biomass, saccharification reaction and sugar analysis of a saccharified supernatant were conducted in the same manner as in Example 11. For a comparative control, only the genus *Trichoderma* filamentous fungus-derived cellulase was used, and saccharification and sugar analysis of a saccharified supernatant were conducted in the same manner. As a result, the saccharification using the enzyme composition containing the β-glucosidase and the genus *Trichoderma* filamentous fungus-derived cellulase increased an accumulated amount of glucose by about 1.8 times and gave no detectable accumulation of cellobiose, compared to the saccharification using only the genus *Trichoderma* filamentous fungus-derived cellulase. Results on glucose/cellobiose obtained by sugar analysis are shown in Table 8.

TABLE 8

| Used enzyme | Enzyme composition containing β-glucosidase and the genus Trichoderma filamentous fungus-derived cellulase | Genus Trichoderma filamentous fungus-derived cellulase (Comparative control) |
|---|---|---|
| Glucose (g/L) | 24.75 | 13.98 |
| Cellobiose (g/L) | Detection limit or less | 5.19 |

Figure 3:
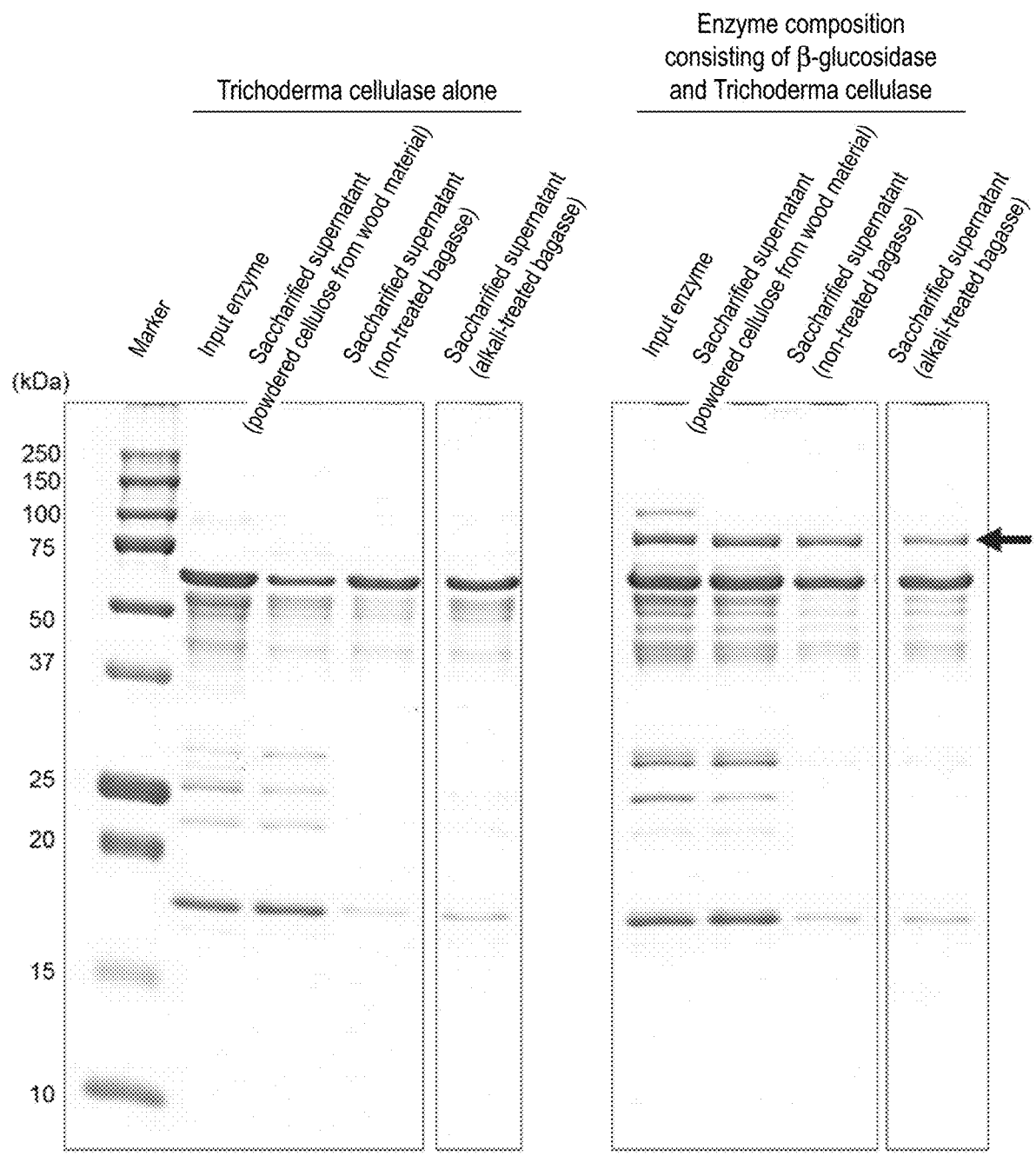
FIG. 3 is a photograph of SDS-PAGE on saccharified supernatants in Example 14.

(Example 14) Confirmation of Remaining Components of the Enzyme Composition Containing the β-Glucosidase and the Genus *Trichoderma* Filamentous Fungus-Derived Cellulase in a Saccharified Supernatant The enzyme composition containing the β-glucosidase and the genus *Trichoderma* filamentous fungus-derived cellulase prepared in Example 10 was used for saccharification reaction. As biomass for saccharification, powdered cellulose from wood material, Arbocel (registered trademark) (J. Rettenmaier & Sohne), alkali-treated bagasse and non-treated bagasse subjected to no pretreatment were used. Saccharification reaction was performed under a reaction condition of 35° C. in the same manner as in Example 11; a sample after 24-hour saccharification reaction was centrifuged under a condition of 10,000×g for 5 minutes; and a saccharified supernatant was collected. 3.5 μL of the saccharified supernatant was taken and mixed with an equal volume of sample buffer; and the mixture was heated at 95° C. for 10 minutes and subjected to SDS-PAGE in accordance with Reference Example 6. For confirmation of bands of the enzyme used for saccharification, the enzyme composition, which was diluted so as to have the same concentration as that in the saccharification reaction solution, was also subjected to SDS-PAGE in the same manner as the saccharified supernatant. For a comparative control, only the genus *Trichoderma* filamentous fungus-derived cellulase obtained by culturing untransformed filamentous fungi of the genus *Trichoderma* was used, and saccharification, collection of a saccharified supernatant and SDS-PAGE were carried out in the same manner. As a result, in all of the cases for saccharification of powdered cellulose from wood material, alkali-treated bagasse and non-treated bagasse, the band for the β-glucosidase of the present invention was clearly observed in the saccharified supernatant with the enzyme composition containing the β-glucosidase and the genus *Trichoderma* filamentous fungus-derived cellulase; and it was confirmed that the β-glucosidase of the present invention could be more easily recovered as a saccharified supernatant than many other cellulase components derived from the genus *Trichoderma* filamentous fungi. In addition, in the saccharification of powdered cellulose from wood material, more bands of more cellulase components derived from the genus *Trichoderma* filamentous fungi were observed in the saccharified supernatant with the enzyme composition containing the β-glucosidase and the genus *Trichoderma* filamentous fungus-derived cellulase, compared to the saccharified supernatant with only the genus *Trichoderma* filamentous fungus-derived cellulase. It was therefore confirmed that when the β-glucosidase of the present invention was used as an enzyme composition in combination with the genus *Trichoderma* filamentous fungus-derived cellulase, the genus *Trichoderma* filamentous fungus-derived cellulase could be also more easily recovered as a saccharified supernatant. A photograph of SDS-PAGE gel is shown in FIG. 3.

(Example 15) Measurement of the Remaining Activity of the Enzyme Composition Containing the β-Glucosidase and the Genus *Trichoderma* Filamentous Fungus-Derived Cellulase in a Saccharified Supernatant of Powdered Cellulose from Wood Material Regarding the saccharified supernatant of powdered cellulose from wood material with the enzyme composition as recovered in Example 14, the enzyme activity was measured in accordance with Reference Examples 2, 3 and 4. The enzyme composition, which was diluted so as to have the same concentration as that in the saccharification reaction solution in Example 14, was also measured for the enzyme activity. The ratio of enzyme activity of a saccharified supernatant when the enzyme activity of the enzyme composition diluted so as to have the same concentration as that in a saccharification reaction solution was taken as 100% was regarded as a remaining activity in the saccharified supernatant, and such activities are shown in Table 9. From the results on the β-glucosidase remaining activity, it was confirmed that the β-glucosidase of the present invention could be more easily recovered as a saccharified supernatant than β-glucosidase derived from the genus *Trichoderma* filamentous fungus. In addition, from the results on the β-xylosidase remaining activity and the cellobiohydrolase/endoglucanase remaining activity, it was confirmed that when the 3-glucosidase of the present invention was used as an enzyme composition together with the genus *Trichoderma* filamentous fungus-derived cellulase, the genus *Trichoderma* filamentous fungus-derived β-xylosidase, cellobiohydrolase and endoglucanase could be easily recovered as a saccharified supernatant.

TABLE 9

| Used enzyme | Enzyme composition containing β-glucosidase and the genus *Trichoderma* filamentous fungus-derived cellulase | Genus *Trichoderma* filamentous fungus-derived cellulase (Comparative control) |
| --- | --- | --- |
| β-glucosidase remaining activity (%) | 98.5 | 77.2 |
| β-xylosidase remaining activity (%) | 29.3 | 1.6 |
| Cellobiohydrolase/ endoglucanase remaining activity (%) | 70.5 | 19.9 |

(Example 16) Measurement of the Remaining Activity of the Enzyme Composition Containing the β-Glucosidase and the Genus *Trichoderma* Filamentous Fungus-Derived Cellulase in a Saccharified Supernatant of Non-Treated Bagasse Regarding the saccharified supernatant of non-treated bagasse with the enzyme composition as recovered in Example 14, the enzyme activity was measured in accordance with Reference Examples 2, 3 and 4. The enzyme composition, which was diluted so as to have the same concentration as that in the saccharification reaction solution in Example 14, was also measured for the enzyme activity. The ratio of enzyme activity of a saccharified supernatant when the enzyme activity of the enzyme composition diluted so as to have the same concentration as that in a saccharification reaction solution was taken as 100% was regarded as a remaining activity in the saccharified supernatant, and such activities are shown in Table 10. From the results on the β-glucosidase remaining activity, it was confirmed that the β-glucosidase of the present invention could be more easily recovered as a saccharified supernatant than β-glucosidase derived from the genus *Trichoderma* filamentous fungus. In addition, from the results on the β-xylosidase remaining activity and the cellobiohydrolase/endoglucanase remaining activity, it was confirmed that when the 3-glucosidase of the present invention was used as an enzyme composition together with the genus *Trichoderma* filamentous fungus-derived cellulase, the genus *Trichoderma* filamentous fungus-derived β-xylosidase, cellobiohydrolase and endoglucanase could be easily recovered as a saccharified supernatant.

TABLE 10

| Used enzyme | Enzyme composition containing β-glucosidase and the genus *Trichoderma* filamentous fungus-derived cellulase | Genus *Trichoderma* filamentous fungus-derived cellulase (Comparative control) |
| --- | --- | --- |
| β-glucosidase remaining activity (%) | 92.0 | 44.2 |
| β-xylosidase remaining activity (%) | 21.9 | 3.4 |
| Cellobiohydrolase/ endoglucanase remaining activity (%) | 42.4 | 37.3 |

(Example 17) Measurement of the Remaining Activity of the Enzyme Composition Containing the β-Glucosidase and the Genus *Trichoderma* Filamentous Fungus-Derived Cellulase in a Saccharified Supernatant of Alkali-Treated Bagasse Regarding the saccharified supernatant of alkali-treated bagasse with the enzyme composition as recovered in Example 14, the enzyme activity was measured in accordance with Reference Examples 2, 3 and 4. The enzyme composition, which was diluted so as to have the same concentration as that in the saccharification reaction solution in Example 14, was also measured for the enzyme activity. The ratio of enzyme activity of a saccharified supernatant when the enzyme activity of the enzyme composition diluted so as to have the same concentration as that in a saccharification reaction solution was taken as 100% was regarded as a remaining activity in the saccharified supernatant, and such activities are shown in Table 11. From the results on the β-glucosidase remaining activity, it was confirmed that the β-glucosidase of the present invention could be more easily recovered as a saccharified supernatant than β-glucosidase derived from the genus *Trichoderma* filamentous fungus. In addition, from the results on the β-xylosidase remaining activity and the cellobiohydrolase/endoglucanase remaining activity, it was confirmed that when the β-glucosidase of the present invention was used as an enzyme composition together with the genus *Trichoderma* filamentous fungus-derived cellulase, the genus *Trichoderma* filamentous fungus-derived β-xylosidase, cellobiohydrolase and endoglucanase could be easily recovered as a saccharified supernatant.

TABLE 11

| Used enzyme | Enzyme composition containing β-glucosidase and the genus *Trichoderma* filamentous fungus-derived cellulase | Genus *Trichoderma* filamentous fungus-derived cellulase (Comparative control) |
| --- | --- | --- |
| β-glucosidase remaining activity (%) | 59.2 | 44.5 |
| β-xylosidase remaining activity (%) | 15.1 | 0.4 |
| Cellobio-hydrolase/endoglucanase remaining activity (%) | 53.0 | 23.3 |

Figure 4:
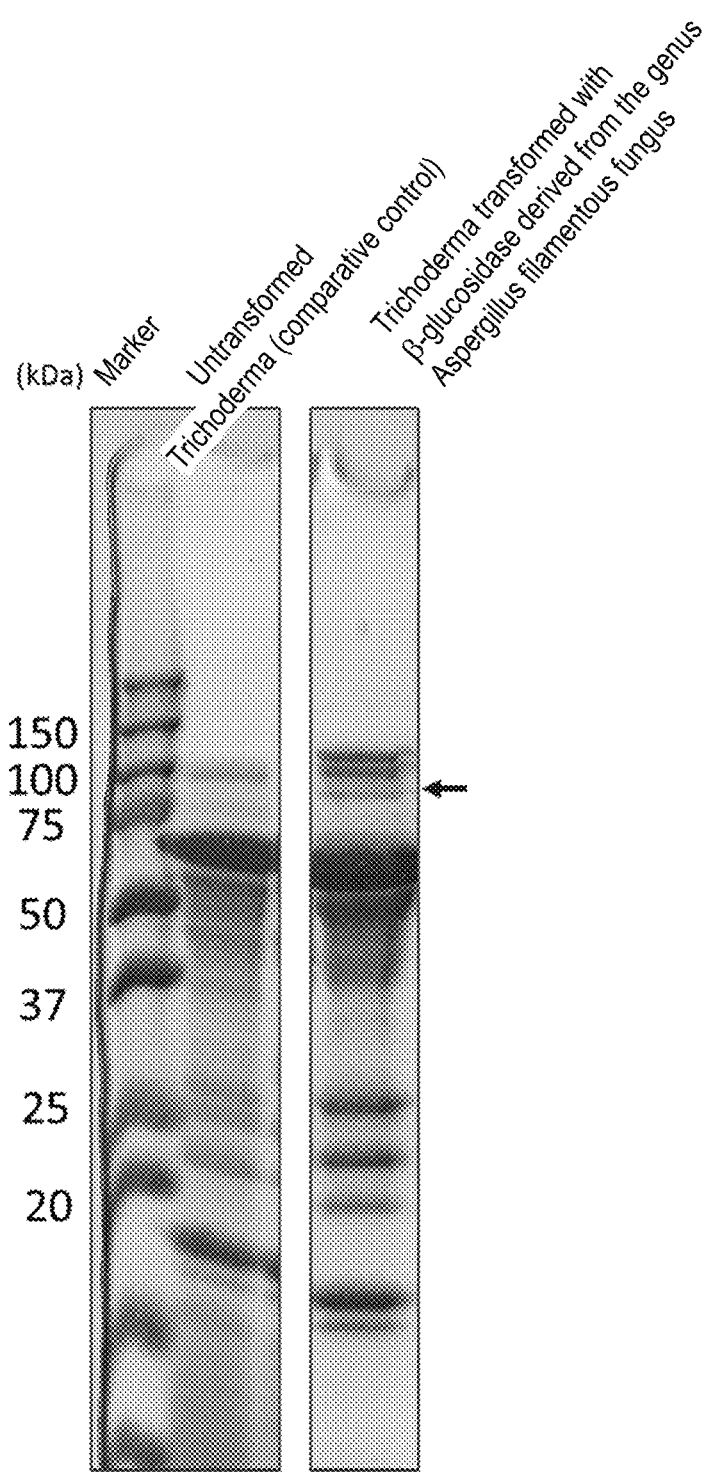
FIG. 4 is a photograph of SDS-PAGE on the genus *Aspergillus* filamentous fungus-derived β-glucosidase β-glucosidase including an amino acid sequence represented by SEQ ID NO: 10) expressed in the genus *Trichoderma* filamentous fungus in Comparative Example 1.

(Comparative Example 1) Production of Filamentous Fungus of the Genus *Trichoderma* Transformed with the β-Glucosidase Gene Derived from the Genus *Aspergillus* Filamentous Fungus, and Production of an Enzyme Composition by Culturing the Transformant In the same manner as in Example 9, a plasmid was designed and produced so as to introduce the nucleotide sequence represented by SEQ ID NO: 11 (nucleotide sequence encoding β-glucosidase gene derived from the genus *Aspergillus* filamentous fungus) into a genome of a host cell, and express and secrete β-glucosidase having the amino acid sequence represented by SEQ ID NO: 10. The plasmid was introduced into an *Agrobacterium tumefaciens* AGL1 strain; *Trichoderma reesei* was infected with the transformed *Agrobacterium*; and a β-glucosidase transformed *Trichoderma* strain was obtained. In the same manner as in Example 10, the above-produced filamentous fungus of the genus *Trichoderma* transformed with the β-glucosidase gene derived from the genus *Aspergillus* filamentous fungus was cultured by the same method as in Reference Example 7; the culture solution after 4 days from the start of culture was centrifuged; a supernatant was filtrated by an ultrafilter membrane to remove fungal bodies; and thereby, an enzyme composition containing the β-glucosidase derived from the genus *Aspergillus* filamentous fungus as expressed in the genus *Trichoderma* filamentous fungus and the genus *Trichoderma* filamentous fungus-derived cellulase was prepared. SDS-PAGE on the enzyme composition was conducted in accordance with Reference Example 6, so that the expressed protein was confirmed. For a comparative control, only the genus *Trichoderma* filamentous fungus-derived cellulase obtained by culturing untransformed genus *Trichoderma* filamentous fungi was used, and culture, collection of a supernatant, filtration of a cultured supernatant and SDS-PAGE were carried out in the same manner. As a result of SDS-PAGE, it was confirmed that β-glucosidase derived from the genus *Aspergillus* filamentous fungus was expressed. A photograph of SDS-PAGE gel is shown in FIG. 4. According to Reference Example 8, the inhibitory action of glucose on the β-glucosidase activity was measured in the enzyme composition containing the genus *Aspergillus* filamentous fungus-derived β-glucosidase and the genus *Trichoderma* filamentous fungus-derived cellulose, and the results were used for comparison with those of Example 18.

(Example 18) Method for Measuring Inhibitory Action of Glucose on the β-Glucosidase Activity In accordance with Reference Example 8, the inhibitory action of glucose on the β-glucosidase activity was measured in enzyme compositions: containing the β-glucosidase and the genus *Trichoderma* filamentous fungus-derived cellulase prepared in Example 10; and the cell-free extract of β-glucosidase mutant gene transformed *E. coli* prepared in Example 5. For a comparative control, only the genus *Trichoderma* filamentous fungus-derived cellulase was used, and the inhibitory action of glucose on the β-glucosidase activity was measured in the same manner. When the β-glucosidase activity under the condition where a reaction solution had a glucose concentration of 0 g/L was standardized as unity, values for the relative activity in the presence of glucose are shown in FIG. 5. In addition, when the β-glucosidase activity under the condition where a reaction solution had a glucose concentration of 0 g/L was standardized as unity, values for the relative activity under the condition of 8 g/L glucose are shown in Table 12; and values for the relative activity under the condition of 20 g/L glucose are shown in Table 13. As a result, both of the enzyme composition containing the β-glucosidase and the genus *Trichoderma* filamentous fungus-derived cellulase, and the cell-free extract of β-glucosidase mutant gene transformed *E. coli* exhibited a smaller decrease of β-glucosidase activity by glucose compared to only the genus *Trichoderma* filamentous fungus-derived cellulase and the enzyme composition of Comparative Example 1 containing the genus *Aspergillus* filamentous fungus-derived β-glucosidase and the genus *Trichoderma* filamentous fungus-derived cellulase. That is, both of the enzyme composition containing β-glucosidase of the present invention and the genus *Trichoderma* filamentous fungus-derived cellulase, and the cell-free extract of β-glucosidase mutant gene transformed *E. coli* were less likely to suffer from inhibition on the β-glucosidase activity by glucose, compared to only the genus *Trichoderma* filamentous fungus-derived cellulase, and the enzyme composition of Comparative Example 1 containing the genus *Aspergillus* filamentous fungus-derived β-glucosidase and the genus *Trichoderma* filamentous fungus-derived cellulase.

TABLE 12

| | BGL activity (relative value) in the presence of 8 g/L glucose when BGL activity in the absence of glucose is taken as unity |
|---|---|
| β-glucosidase of the present invention (SEQ ID NO: 1) (β-glucosidase derived from a protist of the genus *Pseudotrichonympha* and the genus *Trichoderma* filamentous fungus-derived cellulase) | 1.49 |
| β-glucosidase mutant 1 of the present invention (SEQ ID NO: 6) (Cell-free extract of β-glucosidase mutant gene transformed *E. coli*) | 0.71 |
| β-glucosidase mutant 2 of the present invention (SEQ ID NO: 8) (Cell-free extract of β-glucosidase mutant gene transformed *E. coli*) | 0.74 |
| Comparative Example 1: β-glucosidase derived from the genus *Aspergillus* filamentous fungus (enzyme composition containing the genus *Aspergillus* filamentous fungus-derived β-glucosidase and the genus *Trichoderma* filamentous fungus-derived cellulase) | 0.46 |
| Comparative control: BGL derived from the genus *Trichoderma* filamentous fungus (the genus *Trichoderma* filamentous fungus-derived cellulase alone) | 0.09 |

TABLE 13

| | BGL activity (relative value) in the presence of 20 g/L glucose when BGL activity in the absence of glucose is taken as unity |
|---|---|
| β-glucosidase of the present invention (SEQ ID NO: 1) (β-glucosidase derived from a protist of the genus *Pseudotrichonympha* and the genus *Trichoderma* filamentous fungus-derived cellulase) | 0.94 |
| β-glucosidase mutant 1 of the present invention (SEQ ID NO: 6) (Cell-free extract of β-glucosidase mutant gene transformed *E. coli*) | 0.70 |
| β-glucosidase mutant 2 of the present invention (SEQ ID NO: 8) (Cell-free extract of β-glucosidase mutant gene transformed *E. coli*) | 0.72 |
| Comparative Example 1: β-glucosidase derived from the genus *Aspergillus* filamentous fungus (enzyme composition containing the genus *Aspergillus* filamentous fungus-derived β-glucosidase and the genus *Trichoderma* filamentous fungus-derived cellulase) | 0.20 |
| Comparative control: BGL derived from the genus *Trichoderma* filamentous fungus (the genus *Trichoderma* filamentous fungus-derived cellulase alone) | 0.04 |

All publications, patents and patent applications cited in the specification are incorporated herein in the entirety by reference.

The invention claimed is:

1. An enzyme composition comprising a polypeptide that is any one of the following (A) to (C) and a cellulase derived from a filamentous fungus:
   (A) a polypeptide comprising the amino acid sequence of SEQ ID NO: 1;
   (B) a polypeptide comprising the amino acid sequence obtained by substituting, deleting, inserting and/or adding 1-10 amino acids in the amino acid sequence of SEQ ID NO: 1 and having β-glucosidase activity; and
   (C) a polypeptide comprising the amino acid sequence having at least 90% sequence identity with the amino acid sequence of SEQ ID NO: 1 and having β-glucosidase activity.

2. The enzyme composition according to claim 1, wherein the filamentous fungus is a filamentous fungus of the genus *Trichoderma*.

3. A method for producing a sugar solution from cellulose-containing biomass, comprising using the enzyme composition according to claim 1 to produce the sugar solution.

4. The method for producing a sugar solution according to claim 3, comprising the step of recovering the enzyme composition from the sugar solution.

5. The method of claim 3, wherein the filamentous fungus is a filamentous fungus of the genus *Trichoderma*.

6. An enzyme composition comprising a polypeptide that is any one of the following (A) to (C) and a cellulase derived from a filamentous fungus:
   (A) a polypeptide comprising the amino acid sequence of SEQ ID NO: 1;
   (B) a polypeptide comprising the amino acid sequence obtained by substituting, deleting, inserting and/or adding 1-10 amino acids in the amino acid sequence of SEQ ID NO: 1 and having β-glucosidase activity, wherein the polypeptide belongs to a GH3 family; and
   (C) a polypeptide comprising the amino acid sequence having at least 80% sequence identity with the amino acid sequence of SEQ ID NO: 1 and having β-glucosidase activity, wherein the polypeptide belongs to a GH3 family.

7. The enzyme composition according to claim 6, wherein the filamentous fungus is a filamentous fungus of the genus *Trichoderma*.

* * * * *

SEQUENCE LISTING

```
<160> NUMBER OF SEQ ID NOS: 11

<210> SEQ ID NO 1
<211> LENGTH: 727
<212> TYPE: PRT
<213> ORGANISM: Pseudotrichonympha grassii

<400> SEQUENCE: 1

Gln Ile Glu Gly Leu Ile Asn Val Met Thr Leu Glu Glu Lys Val Gly
1               5                   10                  15

Gln Met Ala Gln Leu Ala Ile Asp Leu Phe Ile Asp Val Pro Thr Asp
            20                  25                  30

Thr Val Ile Pro Glu Ala Ala Arg Lys Gly Ile Ile Asp Tyr Lys Ile
        35                  40                  45

Gly Ser Ile Leu Asn Thr Tyr Gly Gly Val Ser His Ser Lys Glu Val
    50                  55                  60

Trp Thr Tyr Ile Asn Ala Glu Phe Tyr Lys Tyr Thr Glu Glu Thr Asp
65                  70                  75                  80

Leu Lys Ile Pro Ile Leu Tyr Gly Leu Asp Ser Ile His Gly Ala Asn
                85                  90                  95

Phe Val Asn Asn Phe Thr Ser Phe Pro Gln Gln Ile Gly Met Ala Ala
            100                 105                 110

Thr Phe Asn Pro Ser Leu Leu Lys Glu Gly Ser Arg Ile Ser Ala Tyr
        115                 120                 125

Glu Thr Arg Ala Ala Ser Val Gly Trp Val Phe Ser Pro Val Met Asp
    130                 135                 140

Leu Gly Leu Asp Pro Arg Trp Pro Arg Ile Trp Glu Gly Phe Gly Glu
145                 150                 155                 160
```

```
Asp Pro Tyr Leu Ser Ser Gln Phe Gly Ile Ala Ser Val His Gly Phe
                165                 170                 175

Gln Gly Lys Asp Pro Asn Leu Ile Asp Glu Phe His Val Ala Ala Cys
            180                 185                 190

Ala Lys His Tyr Leu Ala Tyr Ser Asn Pro Phe Thr Gly Lys Asp Arg
        195                 200                 205

Thr Pro Ala Ile Leu Ser Asp Ile Phe Ile Arg Glu Tyr His Leu Pro
    210                 215                 220

Ser Phe Lys Ala Ala Val Asp Ala Gly Val Ala Ser Val Met Val Asn
225                 230                 235                 240

Ser Gly Leu Ile Asn Gly Ile Pro Thr His Met Asn His Tyr Leu Leu
                245                 250                 255

Thr Thr Val Leu Lys Glu Glu Leu Gly Phe Gln Gly Val Ile Val Thr
            260                 265                 270

Asp Trp Gln Asp Ile Glu Asn Ile His Thr Arg Asp His Leu Ala Pro
        275                 280                 285

Thr Gln Lys Asp Ala Val Lys Leu Ala Ile Asn Ala Gly Ile Asp Met
    290                 295                 300

Ser Met Ile Pro Tyr Asn Tyr Asp Phe Ile Asp Tyr Leu Ile Glu Leu
305                 310                 315                 320

Val His Glu Gly Glu Val Ser Ile Asp Arg Ile Asn Asp Ala Val Arg
                325                 330                 335

Arg Ile Leu Lys Met Lys Ala Lys Met Asn Leu Trp Asp Leu Pro Val
            340                 345                 350

Thr Lys Ser Glu Asp Tyr Pro Glu Phe Gly Ser Glu Ala His Ala Asn
        355                 360                 365

Ala Ser Tyr Thr Ala Ala Ser Glu Ser Ile Thr Leu Leu Lys Asn Glu
    370                 375                 380

Asn Ser Thr Leu Pro Leu Ala Lys Asn Thr Lys Val Leu Val Val Gly
385                 390                 395                 400

Pro Asn Ser Asn Ser His Arg Ser Leu Asn Gly Gly Trp Ser Tyr Ser
                405                 410                 415

Trp Gln Gly Asn Ala Gly Val Gln Tyr Ala Val Gln Tyr Asn Thr Ile
            420                 425                 430

Tyr Gln Ala Ile Gln Lys Val Asn Gly Glu Glu Asn Thr Val Phe Ser
        435                 440                 445

Gln Gly Val Arg Tyr Ile Glu Thr Gly Asn Tyr Tyr Glu Asp Glu Glu
    450                 455                 460

Val Asn Ile Ser Glu Ser Val Ala Leu Ala Arg Asp Val Asp Tyr Ile
465                 470                 475                 480

Ile Leu Ala Leu Gly Glu Asn Thr Tyr Thr Glu Lys Pro Gly Asp Leu
                485                 490                 495

Ser Asp Leu Glu Ile Ser Gln Asn Gln Ile Asp Leu Ala Lys Ala Leu
            500                 505                 510

Ala Ser Thr Gly Lys Pro Ile Ile Leu Val Leu Asn Gln Gly Arg Pro
        515                 520                 525

Arg Ile Ile Ser Arg Ile Glu Gln Leu Val Ser Ala Ile Leu Trp Ile
    530                 535                 540

Tyr Trp Pro Gly Asn Tyr Gly Gly Asp Ala Leu Ala Asp Ile Leu Phe
545                 550                 555                 560

Gly Asp Val Asn Pro Ser Gly Lys Leu Pro Val Thr Tyr Pro Arg Tyr
                565                 570                 575
```

-continued

```
Ser Ala Ser Leu Ile Thr Tyr Trp His Lys Tyr Ala Glu Glu Gln Val
            580                 585                 590

Gly Gln Pro Gly Ala Tyr Asp Tyr Ser Ser Asp Tyr Asn Pro Leu Trp
        595                 600                 605

Glu Phe Gly Tyr Gly Leu Ser Tyr Thr Thr Phe Asn Tyr Ser Asn Leu
    610                 615                 620

Ser Val Pro Ser Thr Ser Gly Met Arg Asp Val Ile Pro Val Ser Val
625                 630                 635                 640

Leu Val Lys Asn Thr Gly Glu Val Ala Gly Lys Glu Val Val Leu Leu
                645                 650                 655

Phe Thr Ser Asp Leu Tyr Ala Ser Leu Ala Pro Asp Val Lys Arg Leu
            660                 665                 670

Arg Lys Phe Thr Lys Ile Leu Leu Gln Pro Gly Glu Glu Gln Leu Val
        675                 680                 685

Ser Phe Asn Leu Thr Ser Ser Asp Leu Ser Phe Ile Asp Ala Gln Ser
    690                 695                 700

Arg Arg Val Thr Glu Thr Gly Asp Phe Glu Ile Lys Ile Gly Gly Leu
705                 710                 715                 720

Lys Gly Lys Val Thr Leu Thr
                725

<210> SEQ ID NO 2
<211> LENGTH: 2184
<212> TYPE: DNA
<213> ORGANISM: Pseudotrichonympha grassii
<220> FEATURE:
<221> NAME/KEY: CDS
<222> LOCATION: (1)..(2184)

<400> SEQUENCE: 2 caa att gaa gga ctt ata aat gta atg aca ttg gaa gaa aag gtt ggt       48
Gln Ile Glu Gly Leu Ile Asn Val Met Thr Leu Glu Glu Lys Val Gly
1               5                   10                  15 caa atg gca caa tta gca att gac tta ttc att gat gtt cca aca gac       96
Gln Met Ala Gln Leu Ala Ile Asp Leu Phe Ile Asp Val Pro Thr Asp
            20                  25                  30 act gtt att cca gaa gca gca aga aaa gga ata att gat tac aaa ata      144
Thr Val Ile Pro Glu Ala Ala Arg Lys Gly Ile Ile Asp Tyr Lys Ile
        35                  40                  45 gga tca att tta aat aca tat ggt gga gta tct cat agt aaa gaa gta      192
Gly Ser Ile Leu Asn Thr Tyr Gly Gly Val Ser His Ser Lys Glu Val
    50                  55                  60 tgg act tat atc aat gca gaa ttc tac aaa tac act gaa gaa aca gat      240
Trp Thr Tyr Ile Asn Ala Glu Phe Tyr Lys Tyr Thr Glu Glu Thr Asp
65                  70                  75                  80 ctt aaa att cct att ctt tat gga tta gac tca att cat ggt gca aac      288
Leu Lys Ile Pro Ile Leu Tyr Gly Leu Asp Ser Ile His Gly Ala Asn
                85                  90                  95 ttt gtt aac aac ttc act tca ttt cct caa caa att gga atg gca gca      336
Phe Val Asn Asn Phe Thr Ser Phe Pro Gln Gln Ile Gly Met Ala Ala
            100                 105                 110 aca ttt aat cct tct ctc ctt aaa gaa gga agc aga atc agt gct tat      384
Thr Phe Asn Pro Ser Leu Leu Lys Glu Gly Ser Arg Ile Ser Ala Tyr
        115                 120                 125 gaa aca aga gca gca tct gtt ggt tgg gtt ttc tct cct gtt atg gat      432
Glu Thr Arg Ala Ala Ser Val Gly Trp Val Phe Ser Pro Val Met Asp
    130                 135                 140 ctt ggt ctt gat cca aga tgg cct cgt att tgg gaa ggt ttt gga gaa      480
Leu Gly Leu Asp Pro Arg Trp Pro Arg Ile Trp Glu Gly Phe Gly Glu
```

```
                                                                       -continued
145             150             155             160
gat cct tat tta agc agt caa ttt gga att gct tct gtt cat gga ttt        528
Asp Pro Tyr Leu Ser Ser Gln Phe Gly Ile Ala Ser Val His Gly Phe
                165             170             175 caa ggt aaa gat cct aat tta att gat gaa ttt cac gtt gct gca tgt        576
Gln Gly Lys Asp Pro Asn Leu Ile Asp Glu Phe His Val Ala Ala Cys
        180             185             190 gct aaa cat tat tta gct tat tct aat cct ttc act gga aaa gac aga        624
Ala Lys His Tyr Leu Ala Tyr Ser Asn Pro Phe Thr Gly Lys Asp Arg
            195             200             205 act cct gct att ttg tct gat att ttc att aga gaa tat cat ctt cct        672
Thr Pro Ala Ile Leu Ser Asp Ile Phe Ile Arg Glu Tyr His Leu Pro
    210             215             220 tct ttt aaa gct gct gtt gat gct ggt gtt gct tct gtt atg gtt aat        720
Ser Phe Lys Ala Ala Val Asp Ala Gly Val Ala Ser Val Met Val Asn
225             230             235             240 tct ggt tta atc aat gga att cca act cat atg aac cat tat ctt ttg        768
Ser Gly Leu Ile Asn Gly Ile Pro Thr His Met Asn His Tyr Leu Leu
                245             250             255 aca act gtt tta aag gaa gaa tta gga ttc caa ggt gta att gtc act        816
Thr Thr Val Leu Lys Glu Glu Leu Gly Phe Gln Gly Val Ile Val Thr
        260             265             270 gat tgg caa gat att gag aat att cac aca aga gat cat ttg gct cca        864
Asp Trp Gln Asp Ile Glu Asn Ile His Thr Arg Asp His Leu Ala Pro
            275             280             285 act cag aaa gat gca gtg aaa tta gca att aat gct gga att gat atg        912
Thr Gln Lys Asp Ala Val Lys Leu Ala Ile Asn Ala Gly Ile Asp Met
    290             295             300 agt atg att cct tat aat tat gat ttc att gat tat ctg att gaa tta        960
Ser Met Ile Pro Tyr Asn Tyr Asp Phe Ile Asp Tyr Leu Ile Glu Leu
305             310             315             320 gtt cat gaa ggt gaa gtt tct att gac aga att aat gat gct gtt aga       1008
Val His Glu Gly Glu Val Ser Ile Asp Arg Ile Asn Asp Ala Val Arg
                325             330             335 aga att ttg aaa atg aaa gca aaa atg aat ttg tgg gat ctt cca gtc       1056
Arg Ile Leu Lys Met Lys Ala Lys Met Asn Leu Trp Asp Leu Pro Val
        340             345             350 act aaa tct gaa gat tat cct gaa ttt ggt tct gaa gct cat gct aat       1104
Thr Lys Ser Glu Asp Tyr Pro Glu Phe Gly Ser Glu Ala His Ala Asn
            355             360             365 gct tct tat act gca gct tct gag tct att acc ctc ctg aaa aat gaa       1152
Ala Ser Tyr Thr Ala Ala Ser Glu Ser Ile Thr Leu Leu Lys Asn Glu
    370             375             380 aat tca act ctt cct ctg gcg aaa aat aca aaa gtt tta gtt gtt ggt       1200
Asn Ser Thr Leu Pro Leu Ala Lys Asn Thr Lys Val Leu Val Val Gly
385             390             395             400 cca aat tca aat tct cat aga tct ttg aat ggt gga tgg tct tat tct       1248
Pro Asn Ser Asn Ser His Arg Ser Leu Asn Gly Gly Trp Ser Tyr Ser
                405             410             415 tgg cag gga aat gct gga gtt caa tat gca gtg caa tat aac act att       1296
Trp Gln Gly Asn Ala Gly Val Gln Tyr Ala Val Gln Tyr Asn Thr Ile
        420             425             430 tac caa gca att cag aag gtt aat gga gaa gaa aat aca gta ttt tct       1344
Tyr Gln Ala Ile Gln Lys Val Asn Gly Glu Glu Asn Thr Val Phe Ser
            435             440             445 caa ggt gtt aga tac ata gaa act gga aat tat tat gaa gat gaa gag       1392
Gln Gly Val Arg Tyr Ile Glu Thr Gly Asn Tyr Tyr Glu Asp Glu Glu
    450             455             460 gtt aat att tca gaa tct gtc gct ctt gct aga gac gtt gat tat ata       1440
```

| | | | | | | | | | | | | | | |
|---|---|---|---|---|---|---|---|---|---|---|---|---|---|---|
| Val | Asn | Ile | Ser | Glu | Ser | Val | Ala | Leu | Ala | Arg | Asp | Val | Asp | Tyr | Ile |
| 465 | | | | 470 | | | | | 475 | | | | | 480 | |

```
att ctt gct ctt ggt gaa aat act tac act gaa aaa cca gga gat ttg      1488
Ile Leu Ala Leu Gly Glu Asn Thr Tyr Thr Glu Lys Pro Gly Asp Leu
                485                 490                 495 agt gat ctt gaa att tct caa aat caa att gat ctt gca aag gct ctt      1536
Ser Asp Leu Glu Ile Ser Gln Asn Gln Ile Asp Leu Ala Lys Ala Leu
            500                 505                 510 gct tca act gga aaa cca atc att tta gtt tta aat caa gga cga cca      1584
Ala Ser Thr Gly Lys Pro Ile Ile Leu Val Leu Asn Gln Gly Arg Pro
        515                 520                 525 aga att att tca aga att gaa caa ctt gtt tct gct att ctt tgg att      1632
Arg Ile Ile Ser Arg Ile Glu Gln Leu Val Ser Ala Ile Leu Trp Ile
    530                 535                 540 tat tgg cca gga aat tat ggt gga gat gca ctt gct gat att ctc ttt      1680
Tyr Trp Pro Gly Asn Tyr Gly Gly Asp Ala Leu Ala Asp Ile Leu Phe
545                 550                 555                 560 gga gat gtc aat cca tct gga aag ttg cct gtt act tat cca aga tat      1728
Gly Asp Val Asn Pro Ser Gly Lys Leu Pro Val Thr Tyr Pro Arg Tyr
                565                 570                 575 tct gca tct tta atc act tat tgg cat aaa tat gca gaa gaa caa gtt      1776
Ser Ala Ser Leu Ile Thr Tyr Trp His Lys Tyr Ala Glu Glu Gln Val
            580                 585                 590 ggt caa cca ggt gca tat gat tat tca tct gat tat aat cct ctt tgg      1824
Gly Gln Pro Gly Ala Tyr Asp Tyr Ser Ser Asp Tyr Asn Pro Leu Trp
        595                 600                 605 gaa ttt ggt tat ggt ctt tct tac acc aca ttt aat tat tca aat ctt      1872
Glu Phe Gly Tyr Gly Leu Ser Tyr Thr Thr Phe Asn Tyr Ser Asn Leu
    610                 615                 620 tct gtt cct tca acc tct ggt atg aga gat gtt att cca gtc tct gtt      1920
Ser Val Pro Ser Thr Ser Gly Met Arg Asp Val Ile Pro Val Ser Val
625                 630                 635                 640 tta gtc aag aat aca ggt gaa gtt gct gga aaa gag gtt gtt ctt ttg      1968
Leu Val Lys Asn Thr Gly Glu Val Ala Gly Lys Glu Val Val Leu Leu
                645                 650                 655 ttc aca agt gat ctt tat gct tct ttg gct cct gat gtg aaa aga ttg      2016
Phe Thr Ser Asp Leu Tyr Ala Ser Leu Ala Pro Asp Val Lys Arg Leu
            660                 665                 670 aga aag ttt act aag att ctt tta caa cca gga gaa gaa caa tta gtg      2064
Arg Lys Phe Thr Lys Ile Leu Leu Gln Pro Gly Glu Glu Gln Leu Val
        675                 680                 685 agt ttt aat tta act agc agt gat ctt tca ttt att gat gcc caa agt      2112
Ser Phe Asn Leu Thr Ser Ser Asp Leu Ser Phe Ile Asp Ala Gln Ser
    690                 695                 700 cgt aga gtc act gaa act ggt gat ttt gaa atc aaa att ggt ggt ctt      2160
Arg Arg Val Thr Glu Thr Gly Asp Phe Glu Ile Lys Ile Gly Gly Leu
705                 710                 715                 720 aag gga aaa gta aca ctt act taa                                      2184
Lys Gly Lys Val Thr Leu Thr
                725

<210> SEQ ID NO 3
<211> LENGTH: 2184
<212> TYPE: DNA
<213> ORGANISM: Artificial
<220> FEATURE:
<223> OTHER INFORMATION: nucleotide sequence having 66% sequence
      identity with nucleotide sequence of SEQ ID NO: 2
<220> FEATURE:
<221> NAME/KEY: CDS
<222> LOCATION: (1)..(2184)
```

<400> SEQUENCE: 3

```
cag atc gag ggc ctg atc aac gtc atg acc ctg gag gag aag gtc ggc      48
Gln Ile Glu Gly Leu Ile Asn Val Met Thr Leu Glu Glu Lys Val Gly
 1               5                  10                  15 cag atg gcc cag ctc gcc atc gac ctg ttc atc gac gtc ccc acc gac      96
Gln Met Ala Gln Leu Ala Ile Asp Leu Phe Ile Asp Val Pro Thr Asp
             20                  25                  30 acc gtc atc ccc gag gcc gcc cgc aag ggc atc atc gac tac aag atc     144
Thr Val Ile Pro Glu Ala Ala Arg Lys Gly Ile Ile Asp Tyr Lys Ile
         35                  40                  45 ggc agc atc ctg aac acc tac ggc ggc gtc agc cac tcc aag gag gtc     192
Gly Ser Ile Leu Asn Thr Tyr Gly Gly Val Ser His Ser Lys Glu Val
 50                  55                  60 tgg acc tac atc aac gcc gag ttc tac aag tac acc gag gag acg gac     240
Trp Thr Tyr Ile Asn Ala Glu Phe Tyr Lys Tyr Thr Glu Glu Thr Asp
 65                  70                  75                  80 ctc aag atc ccc atc ctc tac ggc ctg gac agc atc cac ggc gcc aac     288
Leu Lys Ile Pro Ile Leu Tyr Gly Leu Asp Ser Ile His Gly Ala Asn
                 85                  90                  95 ttc gtc aac aac ttc acc tcc ttc ccc cag cag atc ggc atg gcc gcc     336
Phe Val Asn Asn Phe Thr Ser Phe Pro Gln Gln Ile Gly Met Ala Ala
             100                 105                 110 acc ttc aac ccc tcc ctc ctg aag gag ggc agc cgc atc tcc gcc tac     384
Thr Phe Asn Pro Ser Leu Leu Lys Glu Gly Ser Arg Ile Ser Ala Tyr
         115                 120                 125 gag acg cgc gcc gcc agc gtc ggc tgg gtc ttc tcc ccc gtc atg gac     432
Glu Thr Arg Ala Ala Ser Val Gly Trp Val Phe Ser Pro Val Met Asp
     130                 135                 140 ctc ggc ctg gac ccc cgc tgg ccc cgc atc tgg gag ggc ttc ggc gag     480
Leu Gly Leu Asp Pro Arg Trp Pro Arg Ile Trp Glu Gly Phe Gly Glu
145                 150                 155                 160 gac ccc tac ctc agc agc cag ttc ggc atc gcc agc gtc cac ggc ttc     528
Asp Pro Tyr Leu Ser Ser Gln Phe Gly Ile Ala Ser Val His Gly Phe
                 165                 170                 175 cag ggc aag gac ccc aac ctg atc gac gag ttc cac gtc gcc gcc tgc     576
Gln Gly Lys Asp Pro Asn Leu Ile Asp Glu Phe His Val Ala Ala Cys
             180                 185                 190 gcc aag cac tac ctc gcc tac tcc aac ccc ttc acc ggc aag gac cgc     624
Ala Lys His Tyr Leu Ala Tyr Ser Asn Pro Phe Thr Gly Lys Asp Arg
         195                 200                 205 acc ccc gcc atc ctg agc gac atc ttc atc cgc gag tac cac ctc ccc     672
Thr Pro Ala Ile Leu Ser Asp Ile Phe Ile Arg Glu Tyr His Leu Pro
     210                 215                 220 tcc ttc aag gcc gcc gtg gac gcc ggc gtc gcc agc gtc atg gtc aac     720
Ser Phe Lys Ala Ala Val Asp Ala Gly Val Ala Ser Val Met Val Asn
225                 230                 235                 240 tcc ggc ctc atc aac ggc atc ccc acc cac atg aac cac tac ctc ctg     768
Ser Gly Leu Ile Asn Gly Ile Pro Thr His Met Asn His Tyr Leu Leu
                 245                 250                 255 acc acc gtc ctc aag gag gag ctg ggc ttc cag ggc gtc atc gtc acc     816
Thr Thr Val Leu Lys Glu Glu Leu Gly Phe Gln Gly Val Ile Val Thr
             260                 265                 270 gac tgg cag gac atc gag aac atc cac acc cgc gac cac ctg gcc ccc     864
Asp Trp Gln Asp Ile Glu Asn Ile His Thr Arg Asp His Leu Ala Pro
         275                 280                 285 acc cag aag gac gcc gtc aag ctc gcc atc aac gcc ggc atc gac atg     912
Thr Gln Lys Asp Ala Val Lys Leu Ala Ile Asn Ala Gly Ile Asp Met
     290                 295                 300 agc atg atc ccc tac aac tac gac ttc atc gac tac ctc atc gag ctg     960
```

```
                                                           -continued

Ser Met Ile Pro Tyr Asn Tyr Asp Phe Ile Asp Tyr Leu Ile Glu Leu
305             310                 315                 320 gtc cac gag ggc gag gtc agc atc gac cgc atc aac gac gcc gtc cgc    1008
Val His Glu Gly Glu Val Ser Ile Asp Arg Ile Asn Asp Ala Val Arg
                325                 330                 335 cgc atc ctg aag atg aag gcc aag atg aac ctc tgg gac ctg ccc gtc    1056
Arg Ile Leu Lys Met Lys Ala Lys Met Asn Leu Trp Asp Leu Pro Val
            340                 345                 350 acc aag agc gag gac tac ccc gag ttc ggc agc gag gcc cac gcc aac    1104
Thr Lys Ser Glu Asp Tyr Pro Glu Phe Gly Ser Glu Ala His Ala Asn
        355                 360                 365 gcc tcc tac acc gcc gcc agc gag tcc atc acc ctc ctg aag aac gag    1152
Ala Ser Tyr Thr Ala Ala Ser Glu Ser Ile Thr Leu Leu Lys Asn Glu
    370                 375                 380 aac agc acc ctc ccc ctg gcc aag aac acc aag gtc ctg gtc gtc ggc    1200
Asn Ser Thr Leu Pro Leu Ala Lys Asn Thr Lys Val Leu Val Val Gly
385                 390                 395                 400 ccc aac agc aac tcc cac cgc tcc ctc aac ggc ggc tgg agc tac tcc    1248
Pro Asn Ser Asn Ser His Arg Ser Leu Asn Gly Gly Trp Ser Tyr Ser
                405                 410                 415 tgg cag ggc aac gcc ggc gtc cag tac gcc gtc cag tac aac acc atc    1296
Trp Gln Gly Asn Ala Gly Val Gln Tyr Ala Val Gln Tyr Asn Thr Ile
            420                 425                 430 tac cag gcc atc cag aag gtc aac ggc gag gag aac acc gtc ttc tcc    1344
Tyr Gln Ala Ile Gln Lys Val Asn Gly Glu Glu Asn Thr Val Phe Ser
        435                 440                 445 cag ggc gtc cgc tac atc gag acg ggc aac tac tac gag gac gag gag    1392
Gln Gly Val Arg Tyr Ile Glu Thr Gly Asn Tyr Tyr Glu Asp Glu Glu
    450                 455                 460 gtc aac atc agc gag tcc gtc gcc ctc gcc cgc gac gtg gac tac atc    1440
Val Asn Ile Ser Glu Ser Val Ala Leu Ala Arg Asp Val Asp Tyr Ile
465                 470                 475                 480 atc ctc gcc ctg ggc gag aac acc tac acc gag aag ccc ggc gac ctc    1488
Ile Leu Ala Leu Gly Glu Asn Thr Tyr Thr Glu Lys Pro Gly Asp Leu
                485                 490                 495 agc gac ctg gag atc agc cag aac cag atc gac ctc gcc aag gcc ctg    1536
Ser Asp Leu Glu Ile Ser Gln Asn Gln Ile Asp Leu Ala Lys Ala Leu
            500                 505                 510 gcc agc acc ggc aag ccc atc atc ctc gtc ctg aac cag ggc cgc cct    1584
Ala Ser Thr Gly Lys Pro Ile Ile Leu Val Leu Asn Gln Gly Arg Pro
        515                 520                 525 cgc atc atc agc cgc atc gag cag ctc gtc tcc gcc atc ctg tgg atc    1632
Arg Ile Ile Ser Arg Ile Glu Gln Leu Val Ser Ala Ile Leu Trp Ile
    530                 535                 540 tac tgg cct ggc aac tac ggc ggc gac gcc ctc gcc gac atc ctg ttc    1680
Tyr Trp Pro Gly Asn Tyr Gly Gly Asp Ala Leu Ala Asp Ile Leu Phe
545                 550                 555                 560 ggc gac gtc aac ccc tcc ggc aag ctg ccc gtc acc tac ccc cgc tac    1728
Gly Asp Val Asn Pro Ser Gly Lys Leu Pro Val Thr Tyr Pro Arg Tyr
                565                 570                 575 agc gcc tcc ctc atc acc tac tgg cac aag tac gcc gag gag cag gtc    1776
Ser Ala Ser Leu Ile Thr Tyr Trp His Lys Tyr Ala Glu Glu Gln Val
            580                 585                 590 ggc cag cct ggc gcc tac gac tac agc tcc gac tac aac ccc ctg tgg    1824
Gly Gln Pro Gly Ala Tyr Asp Tyr Ser Ser Asp Tyr Asn Pro Leu Trp
        595                 600                 605 gag ttc ggc tac ggc ctc agc tac acc acc ttc aac tac agc aac ctg    1872
Glu Phe Gly Tyr Gly Leu Ser Tyr Thr Thr Phe Asn Tyr Ser Asn Leu
    610                 615                 620
```

| | | | | | | | | | | | | | | | | |
|---|---|---|---|---|---|---|---|---|---|---|---|---|---|---|---|---|
| tcc | gtc | ccc | agc | acc | tcc | ggc | atg | cgc | gac | gtc | atc | ccc | gtc | tcc | gtc | 1920 |
| Ser | Val | Pro | Ser | Thr | Ser | Gly | Met | Arg | Asp | Val | Ile | Pro | Val | Ser | Val | |
| 625 | | | | | 630 | | | | | 635 | | | | | 640 | |

| | | | | | | | | | | | | | | | | |
|---|---|---|---|---|---|---|---|---|---|---|---|---|---|---|---|---|
| ctc | gtc | aag | aac | acc | ggc | gag | gtc | gcc | ggc | aag | gag | gtc | gtc | ctc | ctg | 1968 |
| Leu | Val | Lys | Asn | Thr | Gly | Glu | Val | Ala | Gly | Lys | Glu | Val | Val | Leu | Leu | |
| | | | | 645 | | | | | 650 | | | | | 655 | | |

| | | | | | | | | | | | | | | | | |
|---|---|---|---|---|---|---|---|---|---|---|---|---|---|---|---|---|
| ttc | acc | agc | gac | ctc | tac | gcc | tcc | ctg | gcc | ccc | gac | gtc | aag | cgc | ctc | 2016 |
| Phe | Thr | Ser | Asp | Leu | Tyr | Ala | Ser | Leu | Ala | Pro | Asp | Val | Lys | Arg | Leu | |
| | | | 660 | | | | | 665 | | | | | 670 | | | |

| | | | | | | | | | | | | | | | | |
|---|---|---|---|---|---|---|---|---|---|---|---|---|---|---|---|---|
| cgc | aag | ttc | acc | aag | atc | ctc | ctc | cag | cct | ggc | gag | gag | cag | ctc | gtc | 2064 |
| Arg | Lys | Phe | Thr | Lys | Ile | Leu | Leu | Gln | Pro | Gly | Glu | Glu | Gln | Leu | Val | |
| | | 675 | | | | | 680 | | | | | 685 | | | | |

| | | | | | | | | | | | | | | | | |
|---|---|---|---|---|---|---|---|---|---|---|---|---|---|---|---|---|
| agc | ttc | aac | ctg | acc | agc | tcc | gac | ctc | agc | ttc | atc | gac | gcc | cag | tcc | 2112 |
| Ser | Phe | Asn | Leu | Thr | Ser | Ser | Asp | Leu | Ser | Phe | Ile | Asp | Ala | Gln | Ser | |
| | | 690 | | | | | 695 | | | | | 700 | | | | |

| | | | | | | | | | | | | | | | | |
|---|---|---|---|---|---|---|---|---|---|---|---|---|---|---|---|---|
| cgc | cgc | gtc | acc | gag | acg | ggc | gac | ttc | gag | atc | aag | atc | ggc | ggc | ctg | 2160 |
| Arg | Arg | Val | Thr | Glu | Thr | Gly | Asp | Phe | Glu | Ile | Lys | Ile | Gly | Gly | Leu | |
| 705 | | | | | 710 | | | | | 715 | | | | | 720 | |

| | | | | | | |
|---|---|---|---|---|---|---|
| aag | ggc | aag | gtc | acc | ctc | acc | taa | 2184 |
| Lys | Gly | Lys | Val | Thr | Leu | Thr | |
| | | | 725 | | | | |

```
<210> SEQ ID NO 4
<211> LENGTH: 6810
<212> TYPE: DNA
<213> ORGANISM: Artificial
<220> FEATURE:
<223> OTHER INFORMATION: plasmid for expression in Trichoderma
      comprising nucleotide sequence of SEQ ID NO: 3

<400> SEQUENCE: 4
```

| | | | | |
|---|---|---|---|---|
| tggcaggata | tattgtggtg | taaacacaga | aacctctttt | gatgtagtta tgcgcatgct | 60 |
| agactgctcc | tgtttcatgt | ggttacaaca | aacagtctga | tcgacttcga atacttggac | 120 |
| tgatgaaggt | tgtacagatt | gctgacagat | gtcgtaatgc | agagcaaggc tgtagattcc | 180 |
| ataaaaccag | ttgcttcgcc | tgctgtggct | ctggagaacc | aaagagacgt gtctcgggag | 240 |
| ggtaagtggt | atcgaatcta | tgagagaagc | ccagtctaag | agaggaccat ctcgccaggg | 300 |
| gaagatgaag | ctggttacaa | ctgatttgtt | ttcccgtctg | ccaccatggt atagagcctg | 360 |
| gaccaatcag | gctaaatcat | tgtatacaat | aagcctagag | aaaacctgaa atctgtcctc | 420 |
| gtcctttgtc | cgttgtctaa | ttatccgtta | ttttcgaacg | atgatacagt atgagttttg | 480 |
| ccgaaatttt | gctaaaggta | ctatcgacgg | gggacacaag | ggttgagtct gtataacggc | 540 |
| tcgaaacaga | agctggtagc | aggaatccag | gcccgcgttt | catttggatt cattttccca | 600 |
| tattcccctt | gcagaaggat | acgacagtag | cattggaaac | cgtaaatgac ggcaaaaagc | 660 |
| atggttctgc | tcagatactc | caagccaacc | tatcgggtcc | tggaggctat ttccaacatc | 720 |
| tcatagccta | acagaaataa | cggaagtcgg | catctgtatc | gctcaaactg accagacgag | 780 |
| cccgccatat | cgaggcagag | ttactctgtg | ttgcaaatcc | aacttataaa gacaacaacc | 840 |
| gcaaactttg | tcttgtcgcc | atcagattgt | tcgccaagca | ccctccccccc cctatcttaa | 900 |
| gtccttcttg | ttgtcccaaa | atgaagctca | gttggcttga | gcggctgcc ttgacggctg | 960 |
| cttcagtcgt | cagcgctcag | atcgagggcc | tgatcaacgt | catgaccctg aggagaagg | 1020 |
| tcggccagat | ggcccagctc | gccatcgacc | tgttcatcga | cgtccccacc gacaccgtca | 1080 |
| tccccgaggc | cgcccgcaag | ggcatcatcg | actacaagat | cggcagcatc ctgaacacct | 1140 |
| acggcggcgt | cagccactcc | aaggaggtct | ggacctacat | caacgccgag ttctacaagt | 1200 |

-continued

```
acaccgagga gacggacctc aagatcccca tcctctacgg cctggacagc atccacggcg   1260
ccaacttcgt caacaacttc acctccttcc cccagcagat cggcatggcc gccaccttca   1320
acccctccct cctgaaggag ggcagccgca tctccgccta cgagacgcgc gccgccagcg   1380
tcggctgggt cttctccccc gtcatggacc tcggcctgga ccccgctgg ccccgcatct    1440 gggagggctt cggcgaggac ccctacctca gcagccagtt cggcatcgcc agcgtccacg   1500
gcttccaggg caaggacccc aacctgatcg acgagttcca cgtcgccgcc tgcgccaagc   1560
actacctcgc ctactccaac cccttcaccg gcaaggaccg caccccgcc atcctgagcg     1620 acatcttcat ccgcgagtac cacctcccct ccttcaaggc cgccgtggac gccggcgtcg   1680
ccagcgtcat ggtcaactcc ggcctcatca cggcatccc cacccacatg aaccactacc    1740
tcctgaccac cgtcctcaag gaggagctgg gcttccaggg cgtcatcgtc accgactggc   1800
aggacatcga gaacatccac acccgcgacc acctggcccc cacccagaag gacgccgtca   1860
agctcgccat caacgccggc atcgacatga gcatgatccc ctacaactac gacttcatcg   1920
actacctcat cgagctggtc cacgagggcg aggtcagcat cgaccgcatc aacgacgccg   1980
tccgccgcat cctgaagatg aaggccaaga tgaacctctg ggacctgccc gtcaccaaga   2040
gcgaggacta ccccgagttc ggcagcgagg cccacgccaa cgcctcctac accgccgcca   2100
gcgagtccat caccctcctg aagaacgaga acagcaccct ccccctggcc aagaacacca   2160
aggtcctggt cgtcggcccc aacagcaact cccaccgctc cctcaacggc ggctggagct   2220
actcctggca gggcaacgcc ggcgtccagt acgccgtcca gtacaacacc atctaccagg   2280
ccatccagaa ggtcaacggc gaggagaaca ccgtcttctc ccagggcgtc cgctacatcg   2340
agacgggcaa ctactacgag gacgaggagg tcaacatcag cgagtccgtc gccctcgccc   2400
gcgacgtgga ctacatcatc ctcgccctgg gcgagaacac ctacaccgag aagcccggcg   2460
acctcagcga cctggagatc agccagaacc agatcgacct cgccaaggcc ctggccagca   2520
ccggcaagcc catcatcctc gtcctgaacc agggccgccc tcgcatcatc agccgcatcg   2580
agcagctcgt ctccgccatc ctgtggatct actggcctgg caactacggc ggcgacgccc   2640
tcgccgacat cctgttcggc gacgtcaacc cctccggcaa gctgcccgtc acctacccc    2700 gctacagcgc ctccctcatc acctactggc acaagtacgc cgaggagcag gtcggccagc   2760
ctggcgccta cgactacagc tccgactaca cccccctgtg ggagttcggc tacgccctca   2820
gctacaccac cttcaactac agcaacctgt ccgtccccag cacctccggc atgcgcgacg   2880
tcatccccgt ctccgtcctc gtcaagaaca ccggcgaggt cgccggcaag gaggtcgtcc   2940
tcctgttcac cagcgacctc tacgcctccc tggcccccga cgtcaagcgc ctccgcaagt   3000
tcaccaagat cctcctccag cctggcgagg agcagctcgt cagcttcaac ctgaccagct   3060
ccgacctcag cttcatcgac gcccagtccc gccgcgtcac cgagacgggc gacttcgaga   3120
tcaagatcgg cggcctgaag ggcaaggtca ccctcaccta aagcgttgac ttgcctctgg   3180
tctgtccaga cggggcacg atagaatgcg ggcacgcagg gagctcgtag acattgggct    3240
taatatataa gacatgctat gttgtatcta cattagcaaa tgacaaacaa atgaaaaaga   3300
acttatcaag cactgtacca aggaagctca ttatgcgtct ggcgggttca aatgatccgt   3360
gataggttat gccagctgat tgtttgcccg cagggttgac accaccaggg gataatggcc   3420
actttcatct gaatcaagga caggagccgt tgatgatttc cagatatcct atcttcatcg   3480
ctagtactaa taacaagtaa gcaaacagcc agctacactc gtacacaccg ctcatgaaaa   3540
cataagacaa agctcaagcc atgtcaagca ccaccccatc gtacacgtac atcttctacc   3600
```

```
aatctgtcca gatgccggct acgtcagcct ccaacccatt gcgatacaat gacggatgtc   3660
gtatagacca tggcaacggc tcccaccacc attgtcactg cgtccaaagt cttctcccac   3720
ctgctctcag caacgccctt gaaatgcagg aatgccggat acatgtagac caatggaatg   3780
caggcaaaag atcccgtcag cgccacaaac ttatccaaat cacttgctcc caccaccgcc   3840
acgccgatgc atgccacaat ggtcaaggcc cggaggccgt tcttcttcca cttgattgcc   3900
gcgctcttct taccagtggc gcgctctccg aaaatcgacg tttccaatat gcggatcgcg   3960
gggaacagct gcacaggctc gccagccagt acggccagcg agtagagaaa ctggactgca   4020
ctagtcatca ttggataggc agattactca gcctgaatga catcaacatg ttacccatga   4080
tacaataggt cacacaaaca agcgctaaga tgcacttggt atgacaagcc cagtagtccg   4140
tttcaaaaga cctagatgat gaactacaac atgaggtgtt gcctcctgat ccagtccaac   4200
tgcaaacgct gatgtatact caatcaagcc tgatgtaaat gctgcgactc gattcgctgg   4260
atatgaagat caaagagagc tctgatgggt ccaatatagc cgggttttgt taggacagtc   4320
caccacaccg atattagaat tggtcaagca ccttatcatt tcatagagat tgcggtttct   4380
agatctacgc caggaccgag caagcccaga tgagaaccga cgcagatttc cttggcacct   4440
gttgcttcag ctgaatcctg gcaatacgag atacctgctt tgaatatttt gaatagctcg   4500
cccgctggag agcatcctga atgcaagtaa caaccgtaga ggctgacacg gcaggtgttg   4560
ctagggagcg tcgtgttcta caaggccaga cgtcttcgcg gttgatatat atgtatgttt   4620
gactgcaggc tgctcagcga cgacagtcaa gttcgccctc gctgcttgtg caataatcgc   4680
agtggggaag ccacaccgtg actcccatct ttcagtaaag ctctgttggt gtttatcagc   4740
aatacacgta atttaaactc gttagcatgg ggctgatagc ttaattaccg tttaccagtg   4800
ccgcggttct gcagctttcc ttggcccgta aaattcggcg aagccagcca atcaccagct   4860
aggcaccagc taaaccctat aattagtctc ttatcaacac catccgctcc cccgggatca   4920
atgaggagaa tgaggggggat gcggggctaa agaagcctac ataaccctca tgccaactcc   4980
cagtttacac tcgtcgagcc aacatcctga ctataagcta acacagaatg aaaaagcctg   5040
aactcaccgc gacgtctgtc gagaagtttc tgatcgaaaa gttcgacagc gtctccgacc   5100
tgatgcagct ctcggagggc gaagaatctc gtgctttcag cttcgatgta ggagggcgtg   5160
gatatgtcct gcgggtaaat agctgcgccg atggtttcta caaagatcgt tatgtttatc   5220
ggcactttgc atcggccgcg ctcccgattc cggaagtgct tgacattggg gaattcagcg   5280
agagcctgac ctattgcatc tcccgccgtg cacagggtgt cacgttgcaa gacctgcctg   5340
aaaccgaact gcccgctgtt ctgcagccgg tcgcggaggc catggatgcg atcgctgcgg   5400
ccgatcttag ccagacgagc gggttcggcc cattcggacc gcaaggaatc ggtcaataca   5460
ctacatggcg tgatttcata tgcgcgattg ctgatcccca tgtgtatcac tggcaaactg   5520
tgatggacga caccgtcagt gcgtccgtcg cgcaggctct cgatgagctg atgctttggg   5580
ccgaggactg ccccgaagtc cggcacctcg tgcacgcgga tttcggctcc aacaatgtcc   5640
tgacggacaa tggccgcata acagcggtca ttgactggag cgaggcgatg ttcggggatt   5700
cccaatacga ggtcgccaac atcttcttct ggaggccgtg gttggcttgt atggagcagc   5760
agacgcgcta cttcgagcgg aggcatccgg agcttgcagg atcgccgcgg ctccgggcgt   5820
atatgctccg cattggtctt gaccaactct atcagagctt ggttgacggc aatttcgatg   5880
atgcagcttg ggcgcagggt cgatgcgacg caatcgtccg atccggagcc gggactgtcg   5940
```

```
ggcgtacaca aatcgcccgc agaagcgcgg ccgtctggac cgatggctgt gtagaagtac    6000
tcgccgatag tggaaaccga cgccccagca ctcgtgggga tcgggagatg ggggaggcta    6060
actgactaat aagtgtcaga tagcaatttg cacaagaaat caataccagc aactgtaaat    6120
aagcgctgaa gtgaccatgc catgctacga aagagcagaa aaaacctgcc gtagaaccg     6180 aagagatatg acacgcttcc atctctcaaa ggaagaatcc cttcagggtt gcgtttccag    6240
tctagaattg acgagaggcg agtcctgggg aaaattggag atgatttgaa tcttggtgtg    6300
ttctccaaac gtcgcatagc agagtgcgcc gactgatgtg aagatggccg tgatgaggag    6360
catgacaaag tagaggaggc ccttgaactg atgaggcttc ttcatactcg actgaattgg    6420
caggatcagg ccaatgccct caaacgtgaa gatcgccgag cccagagtca ggggaaaatc    6480
ggaggggttg aagagcttga cgcttggctc cataccgtgc ctgaccaggc ttcgaatgtc    6540
aaaataccag atgtatacga gtccaatgag gatgaaggcg tccgccacca gagcaaccgg    6600
acccagcttg agatgttgc ggatccaggc taacggaatg agaggagga actgaagcgc      6660 aattaggccc gacacccga aatgaccaag gccgttggtg acagcgtcga ggaaggagaa     6720
gagattttca gcagtgaaga taatgcctga gcagacgaag cccagctgag aaatggcaat    6780
ggaggcgaca ggatatattg gcgggtaaac                                     6810
```

<210> SEQ ID NO 5
<211> LENGTH: 18
<212> TYPE: PRT
<213> ORGANISM: Pseudotrichonympha grassii

<400> SEQUENCE: 5

Val Leu Lys Glu Glu Leu Gly Phe Gln Gly Val Ile Val Thr Asp Trp
1               5                   10                  15

Gln Asp

<210> SEQ ID NO 6
<211> LENGTH: 754
<212> TYPE: PRT
<213> ORGANISM: Artificial
<220> FEATURE:
<223> OTHER INFORMATION: amino acid sequence having 88% sequence
      identity with amino acid sequence of SEQ ID NO: 1

<400> SEQUENCE: 6

Gln Ile Glu Gly Leu Ile Asn Val Met Thr Leu Glu Glu Lys Val Gly
1               5                   10                  15

Gln Met Ala Gln Leu Ala Ile Asp Leu Phe Ile Asp Val Pro Thr Asp
                20                  25                  30

Thr Val Ile Pro Glu Ala Ala Arg Lys Gly Ile Ile Asp Tyr Lys Ile
            35                  40                  45

Gly Ser Ile Leu Asn Thr Tyr Gly Gly Val Ser His Ser Lys Glu Val
        50                  55                  60

Trp Thr Tyr Ile Asn Ala Glu Phe Tyr Lys Tyr Thr Glu Glu Thr Asp
65                  70                  75                  80

Leu Lys Ile Pro Ile Leu Tyr Gly Leu Asp Ser Ile His Gly Ala Asn
                85                  90                  95

Phe Val Asn Asn Phe Thr Ser Phe Pro Gln Gln Ile Gly Met Ala Ala
                100                 105                 110

Thr Phe Asn Pro Ser Leu Leu Lys Glu Gly Ser Arg Ile Ser Ala Tyr
            115                 120                 125

Glu Thr Arg Ala Ala Ser Val Gly Trp Val Phe Ser Pro Val Met Asp

```
                130             135             140
Leu Gly Leu Asp Pro Arg Trp Pro Arg Ile Trp Glu Gly Phe Gly Glu
145                 150                 155                 160

Asp Pro Tyr Leu Ser Ser Gln Phe Gly Ile Ala Ser Val His Gly Phe
                165                 170                 175

Gln Gly Lys Asp Pro Asn Leu Ile Asp Glu Phe His Val Ala Ala Cys
            180                 185                 190

Ala Lys His Tyr Leu Ala Tyr Ser Asn Pro Phe Thr Gly Lys Asp Arg
        195                 200                 205

Thr Pro Ala Ile Leu Ser Asp Ile Phe Ile Arg Glu Tyr His Leu Pro
    210                 215                 220

Ser Phe Lys Ala Ala Val Asp Ala Gly Val Ala Ser Val Met Val Asn
225                 230                 235                 240

Ser Gly Leu Ile Asn Gly Ile Pro Thr His Met Asn His Tyr Leu Leu
                245                 250                 255

Thr Thr Val Leu Lys Glu Glu Leu Gly Phe Gln Gly Val Ile Val Thr
                260                 265                 270

Asp Trp Gln Asp Ile Glu Asn Ile His Thr Arg Asp His Leu Ala Pro
            275                 280                 285

Thr Gln Lys Asp Ala Val Lys Leu Ala Ile Asn Ala Gly Ile Asp Met
        290                 295                 300

Ser Met Ile Pro Tyr Asn Tyr Asp Phe Ile Asp Tyr Leu Ile Glu Leu
305                 310                 315                 320

Val His Glu Gly Glu Val Ser Ile Asp Arg Ile Asn Asp Ala Val Arg
                325                 330                 335

Arg Ile Leu Lys Met Lys Ala Lys Met Asn Leu Trp Asp Leu Pro Val
                340                 345                 350

Thr Lys Ser Glu Asp Tyr Pro Glu Phe Gly Ser Glu Ala His Ala Asn
            355                 360                 365

Ala Ser Tyr Thr Ala Ala Ser Glu Ser Ile Thr Leu Leu Lys Asn Glu
        370                 375                 380

Asn Ser Thr Leu Pro Leu Ala Lys Asn Thr Lys Val Leu Val Val Gly
385                 390                 395                 400

Pro Asn Ser Asn Ser His Arg Ser Leu Asn Gly Gly Trp Ser Tyr Ser
                405                 410                 415

Trp Gln Gly Asn Ala Gly Val Gln Tyr Ala Val Gln Tyr Asn Thr Ile
                420                 425                 430

Tyr Gln Ala Ile Gln Lys Val Asn Gly Glu Glu Asn Thr Val Phe Ser
        435                 440                 445

Gln Gly Val Arg Tyr Ile Glu Thr Gly Asn Tyr Tyr Glu Asp Glu Glu
    450                 455                 460

Val Asn Ile Ser Glu Ser Val Ala Leu Ala Arg Asp Val Asp Tyr Ile
465                 470                 475                 480

Ile Leu Ala Leu Gly Glu Asn Thr Tyr Thr Glu Lys Pro Gly Asp Leu
                485                 490                 495

Ser Asp Leu Glu Ile Ser Gln Asn Gln Ile Asp Leu Ala Lys Ala Leu
            500                 505                 510

Ala Ser Thr Gly Lys Pro Ile Ile Leu Val Leu Asn Gln Gly Arg Pro
        515                 520                 525

Arg Ile Ile Ser Arg Ile Glu Gln Leu Val Ser Ala Ile Leu Trp Ile
    530                 535                 540

Tyr Trp Pro Gly Asn Tyr Gly Gly Asp Ala Leu Ala Asp Ile Leu Phe
545                 550                 555                 560
```

```
Gly Asp Val Asn Pro Ser Gly Lys Leu Pro Val Thr Tyr Pro Arg Tyr
                565                 570                 575

Ser Ala Ser Leu Asn Thr Arg Ile Val Ser Gly Ser Asp Ser Phe
            580                 585                 590

Ser Glu Gly Leu Phe Ile Asp Tyr Lys His Phe Asp Asp Ala Asn Ile
        595                 600                 605

Thr Pro Arg Tyr Glu Phe Gly Tyr Gly Leu Ser Tyr Thr Lys Phe Asn
    610                 615                 620

Tyr Ser Arg Leu Ser Val Leu Ser Thr Ala Lys Ser Gly Pro Ala Thr
625                 630                 635                 640

Gly Ala Val Val Pro Gly Gly Pro Ser Asp Leu Phe Gln Asn Val Ala
                645                 650                 655

Thr Val Thr Val Asp Ile Ala Asn Ser Gly Gln Val Thr Gly Ala Glu
                660                 665                 670

Val Ala Gln Leu Tyr Ile Thr Tyr Pro Ser Ser Ala Pro Arg Thr Pro
                675                 680                 685

Pro Lys Gln Leu Arg Gly Phe Ala Lys Leu Asn Leu Thr Pro Gly Gln
        690                 695                 700

Ser Gly Thr Ala Thr Phe Asn Ile Arg Arg Arg Asp Leu Ser Tyr Trp
705                 710                 715                 720

Asp Thr Ala Ser Gln Lys Trp Val Val Pro Ser Gly Ser Phe Gly Ile
                725                 730                 735

Ser Val Gly Ala Ser Ser Arg Asp Ile Arg Leu Thr Ser Thr Leu Ser
                740                 745                 750

Val Ala

<210> SEQ ID NO 7
<211> LENGTH: 2262
<212> TYPE: DNA
<213> ORGANISM: Artificial
<220> FEATURE:
<223> OTHER INFORMATION: nucleotide sequence having 53% sequence
      identity with nucleotide sequence of SEQ ID NO: 2 (nucleotide
      sequence encoding amino acid sequence of SEQ ID NO: 6)
<220> FEATURE:
<221> NAME/KEY: CDS
<222> LOCATION: (1)..(2262)

<400> SEQUENCE: 7 cag atc gag ggc ctg atc aac gtc atg acc ctg gag gag aag gtc ggc    48
Gln Ile Glu Gly Leu Ile Asn Val Met Thr Leu Glu Glu Lys Val Gly
1               5                   10                  15 cag atg gcc cag ctc gcc atc gac ctg ttc atc gac gtc ccc acc gac    96
Gln Met Ala Gln Leu Ala Ile Asp Leu Phe Ile Asp Val Pro Thr Asp
            20                  25                  30 acc gtc atc ccc gag gcc gcc cgc aag ggc atc atc gac tac aag atc    144
Thr Val Ile Pro Glu Ala Ala Arg Lys Gly Ile Ile Asp Tyr Lys Ile
        35                  40                  45 ggc agc atc ctg aac acc tac ggc ggc gtc agc cac tcc aag gag gtc    192
Gly Ser Ile Leu Asn Thr Tyr Gly Gly Val Ser His Ser Lys Glu Val
    50                  55                  60 tgg acc tac atc aac gcc gag ttc tac aag tac acc gag gag acg gac    240
Trp Thr Tyr Ile Asn Ala Glu Phe Tyr Lys Tyr Thr Glu Glu Thr Asp
65                  70                  75                  80 ctc aag atc ccc atc ctc tac ggc ctg gac agc atc cac ggc gcc aac    288
Leu Lys Ile Pro Ile Leu Tyr Gly Leu Asp Ser Ile His Gly Ala Asn
                85                  90                  95 ttc gtc aac aac ttc acc tcc ttc ccc cag cag atc ggc atg gcc gcc    336
```

-continued

```
              Phe Val Asn Asn Phe Thr Ser Phe Pro Gln Gln Ile Gly Met Ala Ala
                              100                 105                 110 acc ttc aac ccc tcc ctc ctg aag gag ggc agc cgc atc tcc gcc tac           384
Thr Phe Asn Pro Ser Leu Leu Lys Glu Gly Ser Arg Ile Ser Ala Tyr
            115                 120                 125 gag acg cgc gcc gcc agc gtc ggc tgg gtc ttc tcc ccc gtc atg gac           432
Glu Thr Arg Ala Ala Ser Val Gly Trp Val Phe Ser Pro Val Met Asp
        130                 135                 140 ctc ggc ctg gac ccc cgc tgg ccc cgc atc tgg gag ggc ttc ggc gag           480
Leu Gly Leu Asp Pro Arg Trp Pro Arg Ile Trp Glu Gly Phe Gly Glu
145                 150                 155                 160 gac ccc tac ctc agc agc cag ttc ggc atc gcc agc gtc cac ggc ttc           528
Asp Pro Tyr Leu Ser Ser Gln Phe Gly Ile Ala Ser Val His Gly Phe
                165                 170                 175 cag ggc aag gac ccc aac ctg atc gac gag ttc cac gtc gcc gcc tgc           576
Gln Gly Lys Asp Pro Asn Leu Ile Asp Glu Phe His Val Ala Ala Cys
            180                 185                 190 gcc aag cac tac ctc gcc tac tcc aac ccc ttc acc ggc aag gac cgc           624
Ala Lys His Tyr Leu Ala Tyr Ser Asn Pro Phe Thr Gly Lys Asp Arg
        195                 200                 205 acc ccc gcc atc ctg agc gac atc ttc atc cgc gag tac cac ctc ccc           672
Thr Pro Ala Ile Leu Ser Asp Ile Phe Ile Arg Glu Tyr His Leu Pro
    210                 215                 220 tcc ttc aag gcc gcc gtg gac gcc ggc gtc gcc agc gtc atg gtc aac           720
Ser Phe Lys Ala Ala Val Asp Ala Gly Val Ala Ser Val Met Val Asn
225                 230                 235                 240 tcc ggc ctc atc aac ggc atc ccc acc cac atg aac cac tac ctc ctg           768
Ser Gly Leu Ile Asn Gly Ile Pro Thr His Met Asn His Tyr Leu Leu
                245                 250                 255 acc acc gtc ctc aag gag gag ctg ggc ttc cag ggc gtc atc gtc acc           816
Thr Thr Val Leu Lys Glu Glu Leu Gly Phe Gln Gly Val Ile Val Thr
            260                 265                 270 gac tgg cag gac atc gag aac atc cac acc cgc gac cac ctg gcc ccc           864
Asp Trp Gln Asp Ile Glu Asn Ile His Thr Arg Asp His Leu Ala Pro
        275                 280                 285 acc cag aag gac gcc gtc aag ctc gcc atc aac gcc ggc atc gac atg           912
Thr Gln Lys Asp Ala Val Lys Leu Ala Ile Asn Ala Gly Ile Asp Met
    290                 295                 300 agc atg atc ccc tac aac tac gac ttc atc gac tac ctc atc gag ctg           960
Ser Met Ile Pro Tyr Asn Tyr Asp Phe Ile Asp Tyr Leu Ile Glu Leu
305                 310                 315                 320 gtc cac gag ggc gag gtc agc atc gac cgc atc aac gac gcc gtc cgc          1008
Val His Glu Gly Glu Val Ser Ile Asp Arg Ile Asn Asp Ala Val Arg
                325                 330                 335 cgc atc ctg aag atg aag gcc aag atg aac ctc tgg gac ctg ccc gtc          1056
Arg Ile Leu Lys Met Lys Ala Lys Met Asn Leu Trp Asp Leu Pro Val
            340                 345                 350 acc aag agc gag gac tac ccc gag ttc ggc agc gag gcc cac gcc aac          1104
Thr Lys Ser Glu Asp Tyr Pro Glu Phe Gly Ser Glu Ala His Ala Asn
        355                 360                 365 gcc tcc tac acc gcc gcc agc gag tcc atc acc ctc ctg aag aac gag          1152
Ala Ser Tyr Thr Ala Ala Ser Glu Ser Ile Thr Leu Leu Lys Asn Glu
    370                 375                 380 aac agc acc ctc ccc ctg gcc aag aac acc aag gtc ctg gtc gtc ggc          1200
Asn Ser Thr Leu Pro Leu Ala Lys Asn Thr Lys Val Leu Val Val Gly
385                 390                 395                 400 ccc aac agc aac tcc cac cgc tcc ctc aac ggc ggc tgg agc tac tcc          1248
Pro Asn Ser Asn Ser His Arg Ser Leu Asn Gly Gly Trp Ser Tyr Ser
                405                 410                 415
```

|  |  |
|---|---|
| tgg cag ggc aac gcc ggc gtc cag tac gcc gtc cag tac aac acc atc<br>Trp Gln Gly Asn Ala Gly Val Gln Tyr Ala Val Gln Tyr Asn Thr Ile<br>             420                     425                    430 | 1296 |
| tac cag gcc atc cag aag gtc aac ggc gag gag aac acc gtc ttc tcc<br>Tyr Gln Ala Ile Gln Lys Val Asn Gly Glu Glu Asn Thr Val Phe Ser<br>             435                     440                    445 | 1344 |
| cag ggc gtc cgc tac atc gag acg ggc aac tac tac gag gac gag gag<br>Gln Gly Val Arg Tyr Ile Glu Thr Gly Asn Tyr Tyr Glu Asp Glu Glu<br>    450                     455                     460 | 1392 |
| gtc aac atc agc gag tcc gtc gcc ctc gcc cgc gac gtg gac tac atc<br>Val Asn Ile Ser Glu Ser Val Ala Leu Ala Arg Asp Val Asp Tyr Ile<br>465                     470                     475                    480 | 1440 |
| atc ctc gcc ctg ggc gag aac acc tac acc gag aag ccc ggc gac ctc<br>Ile Leu Ala Leu Gly Glu Asn Thr Tyr Thr Glu Lys Pro Gly Asp Leu<br>                     485                     490                    495 | 1488 |
| agc gac ctg gag atc agc cag aac cag atc gac ctc gcc aag gcc ctg<br>Ser Asp Leu Glu Ile Ser Gln Asn Gln Ile Asp Leu Ala Lys Ala Leu<br>         500                     505                     510 | 1536 |
| gcc agc acc ggc aag ccc atc atc ctc gtc ctg aac cag ggc cgc cct<br>Ala Ser Thr Gly Lys Pro Ile Ile Leu Val Leu Asn Gln Gly Arg Pro<br>             515                     520                    525 | 1584 |
| cgc atc atc agc cgc atc gag cag ctc gtc tcc gcc atc ctg tgg atc<br>Arg Ile Ile Ser Arg Ile Glu Gln Leu Val Ser Ala Ile Leu Trp Ile<br>530                     535                     540 | 1632 |
| tac tgg cct ggc aac tac ggc ggc gac gcc ctc gcc gac atc ctg ttc<br>Tyr Trp Pro Gly Asn Tyr Gly Gly Asp Ala Leu Ala Asp Ile Leu Phe<br>545                     550                     555                    560 | 1680 |
| ggc gac gtc aac ccc tcc ggc aag ctg ccc gtc acc tac ccc cgc tac<br>Gly Asp Val Asn Pro Ser Gly Lys Leu Pro Val Thr Tyr Pro Arg Tyr<br>                     565                     570                    575 | 1728 |
| agc gcc tcc ctc aac act cgc atc gtt tcc ggc ggc agt gac agc ttc<br>Ser Ala Ser Leu Asn Thr Arg Ile Val Ser Gly Gly Ser Asp Ser Phe<br>         580                     585                     590 | 1776 |
| agc gag gga ctg ttc atc gac tat aag cac ttc gac gac gcc aat atc<br>Ser Glu Gly Leu Phe Ile Asp Tyr Lys His Phe Asp Asp Ala Asn Ile<br>             595                     600                    605 | 1824 |
| acg ccg cgg tac gag ttc ggc tat gga ctg tct tac acc aag ttc aac<br>Thr Pro Arg Tyr Glu Phe Gly Tyr Gly Leu Ser Tyr Thr Lys Phe Asn<br>610                     615                     620 | 1872 |
| tac tca cgc ctc tcc gtc ttg tcg acc gcc aag tct ggt cct gcg act<br>Tyr Ser Arg Leu Ser Val Leu Ser Thr Ala Lys Ser Gly Pro Ala Thr<br>625                     630                     635                    640 | 1920 |
| ggg gcc gtt gtg ccg gga ggc ccg agt gat ctg ttc cag aat gtc gcg<br>Gly Ala Val Val Pro Gly Gly Pro Ser Asp Leu Phe Gln Asn Val Ala<br>                     645                     650                    655 | 1968 |
| aca gtc acc gtt gac atc gca aac tct ggc caa gtg act ggt gcc gag<br>Thr Val Thr Val Asp Ile Ala Asn Ser Gly Gln Val Thr Gly Ala Glu<br>         660                     665                     670 | 2016 |
| gta gcc cag ctg tac atc acc tac cca tct tca gca ccc agg acc cct<br>Val Ala Gln Leu Tyr Ile Thr Tyr Pro Ser Ser Ala Pro Arg Thr Pro<br>             675                     680                    685 | 2064 |
| ccg aag cag ctg cga ggc ttt gcc aag ctg aac ctc acg cct ggt cag<br>Pro Lys Gln Leu Arg Gly Phe Ala Lys Leu Asn Leu Thr Pro Gly Gln<br>690                     695                     700 | 2112 |
| agc gga aca gca acg ttc aac atc cga cga cga gat ctc agc tac tgg<br>Ser Gly Thr Ala Thr Phe Asn Ile Arg Arg Arg Asp Leu Ser Tyr Trp<br>705                     710                     715                    720 | 2160 |
| gac acg gct tcg cag aaa tgg gtg gtg ccg tcg ggg tcg ttt ggc atc<br>Asp Thr Ala Ser Gln Lys Trp Val Val Pro Ser Gly Ser Phe Gly Ile<br>                     725                     730                    735 | 2208 |

-continued

```
agc gtg gga gcg agc agc cgg gat atc agg ctg acg agc act ctg tcg    2256
Ser Val Gly Ala Ser Ser Arg Asp Ile Arg Leu Thr Ser Thr Leu Ser
                740                 745                 750 gta gcg                                                            2262
Val Ala
```

<210> SEQ ID NO 8
<211> LENGTH: 580
<212> TYPE: PRT
<213> ORGANISM: Artificial
<220> FEATURE:
<223> OTHER INFORMATION: amino acid sequence having 80% sequence identity with amino acid sequence of SEQ ID NO: 1

<400> SEQUENCE: 8

```
Gln Ile Glu Gly Leu Ile Asn Val Met Thr Leu Glu Glu Lys Val Gly
1               5                   10                  15

Gln Met Ala Gln Leu Ala Ile Asp Leu Phe Ile Asp Val Pro Thr Asp
            20                  25                  30

Thr Val Ile Pro Glu Ala Ala Arg Lys Gly Ile Ile Asp Tyr Lys Ile
        35                  40                  45

Gly Ser Ile Leu Asn Thr Tyr Gly Gly Val Ser His Ser Lys Glu Val
    50                  55                  60

Trp Thr Tyr Ile Asn Ala Glu Phe Tyr Lys Tyr Thr Glu Glu Thr Asp
65                  70                  75                  80

Leu Lys Ile Pro Ile Leu Tyr Gly Leu Asp Ser Ile His Gly Ala Asn
                85                  90                  95

Phe Val Asn Asn Phe Thr Ser Phe Pro Gln Gln Ile Gly Met Ala Ala
            100                 105                 110

Thr Phe Asn Pro Ser Leu Leu Lys Glu Gly Ser Arg Ile Ser Ala Tyr
        115                 120                 125

Glu Thr Arg Ala Ala Ser Val Gly Trp Val Phe Ser Pro Val Met Asp
    130                 135                 140

Leu Gly Leu Asp Pro Arg Trp Pro Arg Ile Trp Glu Gly Phe Gly Glu
145                 150                 155                 160

Asp Pro Tyr Leu Ser Ser Gln Phe Gly Ile Ala Ser Val His Gly Phe
                165                 170                 175

Gln Gly Lys Asp Pro Asn Leu Ile Asp Glu Phe His Val Ala Ala Cys
            180                 185                 190

Ala Lys His Tyr Leu Ala Tyr Ser Asn Pro Phe Thr Gly Lys Asp Arg
        195                 200                 205

Thr Pro Ala Ile Leu Ser Asp Ile Phe Ile Arg Glu Tyr His Leu Pro
    210                 215                 220

Ser Phe Lys Ala Ala Val Asp Ala Gly Val Ala Ser Val Met Val Asn
225                 230                 235                 240

Ser Gly Leu Ile Asn Gly Ile Pro Thr His Met Asn His Tyr Leu Leu
                245                 250                 255

Thr Thr Val Leu Lys Glu Glu Leu Gly Phe Gln Gly Val Ile Val Thr
            260                 265                 270

Asp Trp Gln Asp Ile Glu Asn Ile His Thr Arg Asp His Leu Ala Pro
        275                 280                 285

Thr Gln Lys Asp Ala Val Lys Leu Ala Ile Asn Ala Gly Ile Asp Met
    290                 295                 300

Ser Met Ile Pro Tyr Asn Tyr Asp Phe Ile Asp Tyr Leu Ile Glu Leu
305                 310                 315                 320
```

```
Val His Glu Gly Glu Val Ser Ile Asp Arg Ile Asn Asp Ala Val Arg
            325                 330                 335

Arg Ile Leu Lys Met Lys Ala Lys Met Asn Leu Trp Asp Leu Pro Val
        340                 345                 350

Thr Lys Ser Glu Asp Tyr Pro Glu Phe Gly Ser Glu Ala His Ala Asn
    355                 360                 365

Ala Ser Tyr Thr Ala Ala Ser Glu Ser Ile Thr Leu Leu Lys Asn Glu
370                 375                 380

Asn Ser Thr Leu Pro Leu Ala Lys Asn Thr Lys Val Leu Val Val Gly
385                 390                 395                 400

Pro Asn Ser Asn Ser His Arg Ser Leu Asn Gly Gly Trp Ser Tyr Ser
                405                 410                 415

Trp Gln Gly Asn Ala Gly Val Gln Tyr Ala Val Gln Tyr Asn Thr Ile
            420                 425                 430

Tyr Gln Ala Ile Gln Lys Val Asn Gly Glu Asn Thr Val Phe Ser
        435                 440                 445

Gln Gly Val Arg Tyr Ile Glu Thr Gly Asn Tyr Tyr Glu Asp Glu Glu
    450                 455                 460

Val Asn Ile Ser Glu Ser Val Ala Leu Ala Arg Asp Val Asp Tyr Ile
465                 470                 475                 480

Ile Leu Ala Leu Gly Glu Asn Thr Tyr Thr Glu Lys Pro Gly Asp Leu
                485                 490                 495

Ser Asp Leu Glu Ile Ser Gln Asn Gln Ile Asp Leu Ala Lys Ala Leu
            500                 505                 510

Ala Ser Thr Gly Lys Pro Ile Ile Leu Val Leu Asn Gln Gly Arg Pro
        515                 520                 525

Arg Ile Ile Ser Arg Ile Glu Gln Leu Val Ser Ala Ile Leu Trp Ile
    530                 535                 540

Tyr Trp Pro Gly Asn Tyr Gly Gly Asp Ala Leu Ala Asp Ile Leu Phe
545                 550                 555                 560

Gly Asp Val Asn Pro Ser Gly Lys Leu Pro Val Thr Tyr Pro Arg Tyr
                565                 570                 575

Ser Ala Ser Leu
            580

<210> SEQ ID NO 9
<211> LENGTH: 1743
<212> TYPE: DNA
<213> ORGANISM: Artificial
<220> FEATURE:
<223> OTHER INFORMATION: nucleotide sequence having 53% sequence
      identity with nucleotide sequence of SEQ ID NO: 2 (nucleotide
      sequence encoding amino acid sequence of SEQ ID NO: 8)
<220> FEATURE:
<221> NAME/KEY: CDS
<222> LOCATION: (1)..(1743)

<400> SEQUENCE: 9 cag atc gag ggc ctg atc aac gtc atg acc ctg gag gag aag gtc ggc      48
Gln Ile Glu Gly Leu Ile Asn Val Met Thr Leu Glu Glu Lys Val Gly
1               5                   10                  15 cag atg gcc cag ctc gcc atc gac ctg ttc atc gac gtc ccc acc gac      96
Gln Met Ala Gln Leu Ala Ile Asp Leu Phe Ile Asp Val Pro Thr Asp
            20                  25                  30 acc gtc atc ccc gag gcc gcc cgc aag ggc atc atc gac tac aag atc     144
Thr Val Ile Pro Glu Ala Ala Arg Lys Gly Ile Ile Asp Tyr Lys Ile
        35                  40                  45 ggc agc atc ctg aac acc tac ggc ggc gtc agc cac tcc aag gag gtc     192
```

```
Gly Ser Ile Leu Asn Thr Tyr Gly Gly Val Ser His Ser Lys Glu Val
    50              55                  60 tgg acc tac atc aac gcc gag ttc tac aag tac acc gag gag acg gac    240
Trp Thr Tyr Ile Asn Ala Glu Phe Tyr Lys Tyr Thr Glu Glu Thr Asp
65              70                  75                  80 ctc aag atc ccc atc ctc tac ggc ctg gac agc atc cac ggc gcc aac    288
Leu Lys Ile Pro Ile Leu Tyr Gly Leu Asp Ser Ile His Gly Ala Asn
                85                  90                  95 ttc gtc aac aac ttc acc tcc ttc ccc cag cag atc ggc atg gcc gcc    336
Phe Val Asn Asn Phe Thr Ser Phe Pro Gln Gln Ile Gly Met Ala Ala
            100                 105                 110 acc ttc aac ccc tcc ctc ctg aag gag ggc agc cgc atc tcc gcc tac    384
Thr Phe Asn Pro Ser Leu Leu Lys Glu Gly Ser Arg Ile Ser Ala Tyr
        115                 120                 125 gag acg cgc gcc gcc agc gtc ggc tgg gtc ttc tcc ccc gtc atg gac    432
Glu Thr Arg Ala Ala Ser Val Gly Trp Val Phe Ser Pro Val Met Asp
    130                 135                 140 ctc ggc ctg gac ccc cgc tgg ccc cgc atc tgg gag ggc ttc ggc gag    480
Leu Gly Leu Asp Pro Arg Trp Pro Arg Ile Trp Glu Gly Phe Gly Glu
145                 150                 155                 160 gac ccc tac ctc agc agc cag ttc ggc atc gcc agc gtc cac ggc ttc    528
Asp Pro Tyr Leu Ser Ser Gln Phe Gly Ile Ala Ser Val His Gly Phe
                165                 170                 175 cag ggc aag gac ccc aac ctg atc gac gag ttc cac gtc gcc gcc tgc    576
Gln Gly Lys Asp Pro Asn Leu Ile Asp Glu Phe His Val Ala Ala Cys
            180                 185                 190 gcc aag cac tac ctc gcc tac tcc aac ccc ttc acc ggc aag gac cgc    624
Ala Lys His Tyr Leu Ala Tyr Ser Asn Pro Phe Thr Gly Lys Asp Arg
        195                 200                 205 acc ccc gcc atc ctg agc gac atc ttc atc cgc gag tac cac ctc ccc    672
Thr Pro Ala Ile Leu Ser Asp Ile Phe Ile Arg Glu Tyr His Leu Pro
    210                 215                 220 tcc ttc aag gcc gcc gtg gac gcc ggc gtc gcc agc gtc atg gtc aac    720
Ser Phe Lys Ala Ala Val Asp Ala Gly Val Ala Ser Val Met Val Asn
225                 230                 235                 240 tcc ggc ctc atc aac ggc atc ccc acc cac atg aac cac tac ctc ctg    768
Ser Gly Leu Ile Asn Gly Ile Pro Thr His Met Asn His Tyr Leu Leu
                245                 250                 255 acc acc gtc ctc aag gag gag ctg ggc ttc cag ggc gtc atc gtc acc    816
Thr Thr Val Leu Lys Glu Glu Leu Gly Phe Gln Gly Val Ile Val Thr
            260                 265                 270 gac tgg cag gac atc gag aac atc cac acc cgc gac cac ctg gcc ccc    864
Asp Trp Gln Asp Ile Glu Asn Ile His Thr Arg Asp His Leu Ala Pro
        275                 280                 285 acc cag aag gac gcc gtc aag ctc gcc atc aac gcc ggc atc gac atg    912
Thr Gln Lys Asp Ala Val Lys Leu Ala Ile Asn Ala Gly Ile Asp Met
    290                 295                 300 agc atg atc ccc tac aac tac gac ttc atc gac tac ctc atc gag ctg    960
Ser Met Ile Pro Tyr Asn Tyr Asp Phe Ile Asp Tyr Leu Ile Glu Leu
305                 310                 315                 320 gtc cac gag ggc gag gtc agc atc gac cgc atc aac gac gcc gtc cgc    1008
Val His Glu Gly Glu Val Ser Ile Asp Arg Ile Asn Asp Ala Val Arg
                325                 330                 335 cgc atc ctg aag atg aag gcc aag atg aac ctc tgg gac ctg ccc gtc    1056
Arg Ile Leu Lys Met Lys Ala Lys Met Asn Leu Trp Asp Leu Pro Val
            340                 345                 350 acc aag agc gag gac tac ccc gag ttc ggc agc gag gcc cac gcc aac    1104
Thr Lys Ser Glu Asp Tyr Pro Glu Phe Gly Ser Glu Ala His Ala Asn
        355                 360                 365
```

| | | | | | | | | | | | | | | | |
|---|---|---|---|---|---|---|---|---|---|---|---|---|---|---|---|
| gcc | tcc | tac | acc | gcc | gcc | agc | gag | tcc | atc | acc | ctc | ctg | aag | aac | gag | 1152 |
| Ala | Ser | Tyr | Thr | Ala | Ala | Ser | Glu | Ser | Ile | Thr | Leu | Leu | Lys | Asn | Glu |
| | 370 | | | | 375 | | | | | 380 | | | | | | gcc tcc tac acc gcc gcc agc gag tcc atc acc ctc ctg aag aac gag    1152
Ala Ser Tyr Thr Ala Ala Ser Glu Ser Ile Thr Leu Leu Lys Asn Glu
    370             375                 380 aac agc acc ctc ccc ctg gcc aag aac acc aag gtc ctg gtc gtc ggc    1200
Asn Ser Thr Leu Pro Leu Ala Lys Asn Thr Lys Val Leu Val Val Gly
385             390                 395                 400 ccc aac agc aac tcc cac cgc tcc ctc aac ggc ggc tgg agc tac tcc    1248
Pro Asn Ser Asn Ser His Arg Ser Leu Asn Gly Gly Trp Ser Tyr Ser
            405                 410                 415 tgg cag ggc aac gcc ggc gtc cag tac gcc gtc cag tac aac acc atc    1296
Trp Gln Gly Asn Ala Gly Val Gln Tyr Ala Val Gln Tyr Asn Thr Ile
                420                 425                 430 tac cag gcc atc cag aag gtc aac ggc gag gag aac acc gtc ttc tcc    1344
Tyr Gln Ala Ile Gln Lys Val Asn Gly Glu Glu Asn Thr Val Phe Ser
        435                 440                 445 cag ggc gtc cgc tac atc gag acg ggc aac tac tac gag gac gag gag    1392
Gln Gly Val Arg Tyr Ile Glu Thr Gly Asn Tyr Tyr Glu Asp Glu Glu
    450                 455                 460 gtc aac atc agc gag tcc gtc gcc ctc gcc cgc gac gtg gac tac atc    1440
Val Asn Ile Ser Glu Ser Val Ala Leu Ala Arg Asp Val Asp Tyr Ile
465                 470                 475                 480 atc ctc gcc ctg ggc gag aac acc tac acc gag aag ccc ggc gac ctc    1488
Ile Leu Ala Leu Gly Glu Asn Thr Tyr Thr Glu Lys Pro Gly Asp Leu
                485                 490                 495 agc gac ctg gag atc agc cag aac cag atc gac ctc gcc aag gcc ctg    1536
Ser Asp Leu Glu Ile Ser Gln Asn Gln Ile Asp Leu Ala Lys Ala Leu
            500                 505                 510 gcc agc acc ggc aag ccc atc atc ctc gtc ctg aac cag ggc cgc cct    1584
Ala Ser Thr Gly Lys Pro Ile Ile Leu Val Leu Asn Gln Gly Arg Pro
        515                 520                 525 cgc atc atc agc cgc atc gag cag ctc gtc tcc gcc atc ctg tgg atc    1632
Arg Ile Ile Ser Arg Ile Glu Gln Leu Val Ser Ala Ile Leu Trp Ile
    530                 535                 540 tac tgg cct ggc aac tac ggc ggc gac gcc ctc gcc gac atc ctg ttc    1680
Tyr Trp Pro Gly Asn Tyr Gly Gly Asp Ala Leu Ala Asp Ile Leu Phe
545                 550                 555                 560 ggc gac gtc aac ccc tcc ggc aag ctg ccc gtc acc tac ccc cgc tac    1728
Gly Asp Val Asn Pro Ser Gly Lys Leu Pro Val Thr Tyr Pro Arg Tyr
                565                 570                 575 agc gcc tcc ctc tga                                                1743
Ser Ala Ser Leu
            580

<210> SEQ ID NO 10
<211> LENGTH: 841
<212> TYPE: PRT
<213> ORGANISM: Aspergillus aculeatus

<400> SEQUENCE: 10

Asp Glu Leu Ala Phe Ser Pro Pro Phe Tyr Pro Ser Pro Trp Ala Asn
1               5                   10                  15

Gly Gln Gly Glu Trp Ala Glu Ala Tyr Gln Arg Ala Val Ala Ile Val
                20                  25                  30

Ser Gln Met Thr Leu Asp Glu Lys Val Asn Leu Thr Thr Gly Thr Gly
            35                  40                  45

Trp Glu Leu Glu Lys Cys Val Gly Gln Thr Gly Gly Val Pro Arg Leu
        50                  55                  60

Asn Ile Gly Gly Met Cys Leu Gln Asp Ser Pro Leu Gly Ile Arg Asp
65                  70                  75                  80

```
Ser Asp Tyr Asn Ser Ala Phe Pro Ala Gly Val Asn Val Ala Ala Thr
                85                  90                  95

Trp Asp Lys Asn Leu Ala Tyr Leu Arg Gly Gln Ala Met Gly Gln Glu
               100                 105                 110

Phe Ser Asp Lys Gly Ile Asp Val Gln Leu Gly Pro Ala Ala Gly Pro
               115                 120                 125

Leu Gly Arg Ser Pro Asp Gly Arg Asn Trp Glu Gly Phe Ser Pro
130                 135                 140

Asp Pro Ala Leu Thr Gly Val Leu Phe Ala Glu Thr Ile Lys Gly Ile
145                 150                 155                 160

Gln Asp Ala Gly Val Val Ala Thr Ala Lys His Tyr Ile Leu Asn Glu
                165                 170                 175

Gln Glu His Phe Arg Gln Val Ala Glu Ala Ala Gly Tyr Gly Phe Asn
                180                 185                 190

Ile Ser Asp Thr Ile Ser Ser Asn Val Asp Asp Lys Thr Ile His Glu
                195                 200                 205

Met Tyr Leu Trp Pro Phe Ala Asp Ala Val Arg Ala Gly Val Gly Ala
    210                 215                 220

Ile Met Cys Ser Tyr Asn Gln Ile Asn Asn Ser Tyr Gly Cys Gln Asn
225                 230                 235                 240

Ser Tyr Thr Leu Asn Lys Leu Leu Lys Ala Glu Leu Gly Phe Gln Gly
                245                 250                 255

Phe Val Met Ser Asp Trp Gly Ala His His Ser Gly Val Gly Ser Ala
                260                 265                 270

Leu Ala Gly Leu Asp Met Ser Met Pro Gly Asp Ile Thr Phe Asp Ser
                275                 280                 285

Ala Thr Ser Phe Trp Gly Thr Asn Leu Thr Ile Ala Val Leu Asn Gly
    290                 295                 300

Thr Val Pro Gln Trp Arg Val Asp Asp Met Ala Val Arg Ile Met Ala
305                 310                 315                 320

Ala Tyr Tyr Lys Val Gly Arg Asp Arg Leu Tyr Gln Pro Pro Asn Phe
                325                 330                 335

Ser Ser Trp Thr Arg Asp Glu Tyr Gly Phe Lys Tyr Phe Tyr Pro Gln
                340                 345                 350

Glu Gly Pro Tyr Glu Lys Val Asn His Phe Val Asn Val Gln Arg Asn
                355                 360                 365

His Ser Glu Val Ile Arg Lys Leu Gly Ala Asp Ser Thr Val Leu Leu
                370                 375                 380

Lys Asn Asn Asn Ala Leu Pro Leu Thr Gly Lys Glu Arg Lys Val Ala
385                 390                 395                 400

Ile Leu Gly Glu Asp Ala Gly Ser Asn Ser Tyr Gly Ala Asn Gly Cys
                405                 410                 415

Ser Asp Arg Gly Cys Asp Asn Gly Thr Leu Ala Met Ala Trp Gly Ser
                420                 425                 430

Gly Thr Ala Glu Phe Pro Tyr Leu Val Thr Pro Glu Gln Ala Ile Gln
                435                 440                 445

Ala Glu Val Leu Lys His Lys Gly Ser Val Tyr Ala Ile Thr Asp Asn
450                 455                 460

Trp Ala Leu Ser Gln Val Glu Thr Leu Ala Lys Gln Ala Ser Val Ser
465                 470                 475                 480

Leu Val Phe Val Asn Ser Asp Ala Gly Glu Gly Tyr Ile Ser Val Asp
                485                 490                 495

Gly Asn Glu Gly Asp Arg Asn Asn Leu Thr Leu Trp Lys Asn Gly Asp
```

```
                500             505             510
Asn Leu Ile Lys Ala Ala Asn Asn Cys Asn Asn Thr Ile Val Val
        515                 520             525

Ile His Ser Val Gly Pro Val Leu Val Asp Glu Trp Tyr Asp His Pro
    530                 535             540

Asn Val Thr Ala Ile Leu Trp Ala Gly Leu Pro Gly Gln Glu Ser Gly
545                 550             555             560

Asn Ser Leu Ala Asp Val Leu Tyr Gly Arg Val Asn Pro Gly Ala Lys
                565             570             575

Ser Pro Phe Thr Trp Gly Lys Thr Arg Glu Ala Tyr Gly Asp Tyr Leu
            580             585             590

Val Arg Glu Leu Asn Asn Gly Asn Gly Ala Pro Gln Asp Asp Phe Ser
        595             600             605

Glu Gly Val Phe Ile Asp Tyr Arg Gly Phe Asp Lys Arg Asn Glu Thr
    610             615             620

Pro Ile Tyr Glu Phe Gly His Gly Leu Ser Tyr Thr Thr Phe Asn Tyr
625             630             635             640

Ser Gly Leu His Ile Gln Val Leu Asn Ala Ser Ser Asn Ala Gln Val
                645             650             655

Ala Thr Glu Thr Gly Ala Ala Pro Thr Phe Gly Gln Val Gly Asn Ala
            660             665             670

Ser Asp Tyr Val Tyr Pro Glu Gly Leu Thr Arg Ile Ser Lys Phe Ile
        675             680             685

Tyr Pro Trp Leu Asn Ser Thr Asp Leu Lys Ala Ser Ser Gly Asp Pro
    690             695             700

Tyr Tyr Gly Val Asp Thr Ala Glu His Val Pro Glu Gly Ala Thr Asp
705             710             715             720

Gly Ser Pro Gln Pro Val Leu Pro Ala Gly Gly Ser Gly Gly Asn
                725             730             735

Pro Arg Leu Tyr Asp Glu Leu Ile Arg Val Ser Val Thr Val Lys Asn
            740             745             750

Thr Gly Arg Val Ala Gly Asp Ala Val Pro Gln Leu Tyr Val Ser Leu
        755             760             765

Gly Gly Pro Asn Glu Pro Lys Val Val Leu Arg Lys Phe Asp Arg Leu
    770             775             780

Thr Leu Lys Pro Ser Glu Glu Thr Val Trp Thr Thr Thr Leu Thr Arg
785             790             795             800

Arg Asp Leu Ser Asn Trp Asp Val Ala Ala Gln Asp Trp Val Ile Thr
                805             810             815

Ser Tyr Pro Lys Lys Val His Val Gly Ser Ser Arg Gln Leu Pro
            820             825             830

Leu His Ala Ala Leu Pro Lys Val Gln
        835             840

<210> SEQ ID NO 11
<211> LENGTH: 2526
<212> TYPE: DNA
<213> ORGANISM: Aspergillus aculeatus
<220> FEATURE:
<221> NAME/KEY: CDS
<222> LOCATION: (1)..(2526)

<400> SEQUENCE: 11 gat gaa ctg gcg ttc tct cct cct ttc tac ccc tct ccg tgg gcc aat      48
Asp Glu Leu Ala Phe Ser Pro Pro Phe Tyr Pro Ser Pro Trp Ala Asn
1               5                   10                  15
```

```
ggc cag gga gag tgg gcg gaa gcc tac cag cgt gca gtg gcc att gta         96
Gly Gln Gly Glu Trp Ala Glu Ala Tyr Gln Arg Ala Val Ala Ile Val
             20                  25                  30 tcc cag atg act ctg gat gag aag gtc aac ctg acc acc gga act gga        144
Ser Gln Met Thr Leu Asp Glu Lys Val Asn Leu Thr Thr Gly Thr Gly
         35                  40                  45 tgg gag ctg gag aag tgc gtc ggt cag act ggt ggt gtc cca aga ctg        192
Trp Glu Leu Glu Lys Cys Val Gly Gln Thr Gly Gly Val Pro Arg Leu
     50                  55                  60 aac atc ggt ggc atg tgt ctt cag gac agt ccc ttg gga att cgt gat        240
Asn Ile Gly Gly Met Cys Leu Gln Asp Ser Pro Leu Gly Ile Arg Asp
65                  70                  75                  80 agt gac tac aat tcg gct ttc cct gct ggt gtc aac gtt gct gcg aca        288
Ser Asp Tyr Asn Ser Ala Phe Pro Ala Gly Val Asn Val Ala Ala Thr
                 85                  90                  95 tgg gac aag aac ctt gct tat cta cgt ggt cag gct atg ggt caa gag        336
Trp Asp Lys Asn Leu Ala Tyr Leu Arg Gly Gln Ala Met Gly Gln Glu
            100                 105                 110 ttc agt gac aaa gga att gat gtt caa ttg gga ccg gcc gcg ggt ccc        384
Phe Ser Asp Lys Gly Ile Asp Val Gln Leu Gly Pro Ala Ala Gly Pro
        115                 120                 125 ctc ggc agg agc cct gat gga ggt cgc aac tgg gaa ggt ttc tct cca        432
Leu Gly Arg Ser Pro Asp Gly Gly Arg Asn Trp Glu Gly Phe Ser Pro
    130                 135                 140 gac ccg gct ctt act ggt gtg ctc ttt gcg gag acg att aag ggt att        480
Asp Pro Ala Leu Thr Gly Val Leu Phe Ala Glu Thr Ile Lys Gly Ile
145                 150                 155                 160 caa gac gct ggt gtc gtg gcg aca gcc aag cat tac att ctc aat gag        528
Gln Asp Ala Gly Val Val Ala Thr Ala Lys His Tyr Ile Leu Asn Glu
                165                 170                 175 caa gag cat ttc cgc cag gtc gca gag gct gcg ggc tac gga ttc aat        576
Gln Glu His Phe Arg Gln Val Ala Glu Ala Ala Gly Tyr Gly Phe Asn
            180                 185                 190 atc tcc gac acg atc agc tct aac gtt gat gac aag acc att cat gaa        624
Ile Ser Asp Thr Ile Ser Ser Asn Val Asp Asp Lys Thr Ile His Glu
        195                 200                 205 atg tac ctc tgg ccc ttc gcg gat gcc gtt cgc gcc ggc gtt ggc gcc        672
Met Tyr Leu Trp Pro Phe Ala Asp Ala Val Arg Ala Gly Val Gly Ala
    210                 215                 220 atc atg tgt tcc tac aac cag atc aac aac agc tac ggt tgc cag aac        720
Ile Met Cys Ser Tyr Asn Gln Ile Asn Asn Ser Tyr Gly Cys Gln Asn
225                 230                 235                 240 agt tac act ctg aac aag ctt ctg aag gcc gag ctc ggc ttc cag ggc        768
Ser Tyr Thr Leu Asn Lys Leu Leu Lys Ala Glu Leu Gly Phe Gln Gly
                245                 250                 255 ttt gtg atg tct gac tgg ggt gct cac cac agt ggt gtt ggc tct gct        816
Phe Val Met Ser Asp Trp Gly Ala His His Ser Gly Val Gly Ser Ala
            260                 265                 270 ttg gcc ggc ttg gat atg tca atg cct ggc gat atc acc ttc gat tct        864
Leu Ala Gly Leu Asp Met Ser Met Pro Gly Asp Ile Thr Phe Asp Ser
        275                 280                 285 gcc act agt ttc tgg ggt acc aac ctg acc att gct gtg ctc aac ggt        912
Ala Thr Ser Phe Trp Gly Thr Asn Leu Thr Ile Ala Val Leu Asn Gly
    290                 295                 300 acc gtc ccg cag tgg cgc gtt gac gac atg gct gtc cgt atc atg gct        960
Thr Val Pro Gln Trp Arg Val Asp Asp Met Ala Val Arg Ile Met Ala
305                 310                 315                 320 gcc tac tac aag gtt ggc cgc gac cgc ctg tac cag ccg cct aac ttc       1008
Ala Tyr Tyr Lys Val Gly Arg Asp Arg Leu Tyr Gln Pro Pro Asn Phe
```

```
                    325                 330                 335
agc tcc tgg act cgc gat gaa tac ggc ttc aag tat ttc tac ccc cag    1056
Ser Ser Trp Thr Arg Asp Glu Tyr Gly Phe Lys Tyr Phe Tyr Pro Gln
        340                 345                 350 gaa ggg ccc tat gag aag gtc aat cac ttt gtc aat gtg cag cgc aac    1104
Glu Gly Pro Tyr Glu Lys Val Asn His Phe Val Asn Val Gln Arg Asn
            355                 360                 365 cac agc gag gtt att cgc aag ttg gga gca gac agt act gtt cta ctg    1152
His Ser Glu Val Ile Arg Lys Leu Gly Ala Asp Ser Thr Val Leu Leu
370                 375                 380 aag aac aac aat gcc ctg ccg ctg acc gga aag gag cgc aaa gtt gcg    1200
Lys Asn Asn Asn Ala Leu Pro Leu Thr Gly Lys Glu Arg Lys Val Ala
385                 390                 395                 400 atc ctg ggt gaa gat gct gga tcc aac tcg tac ggt gcc aat ggc tgc    1248
Ile Leu Gly Glu Asp Ala Gly Ser Asn Ser Tyr Gly Ala Asn Gly Cys
                405                 410                 415 tct gac cgt ggc tgt gac aac ggt act ctt gct atg gct tgg ggt agc    1296
Ser Asp Arg Gly Cys Asp Asn Gly Thr Leu Ala Met Ala Trp Gly Ser
            420                 425                 430 ggc act gcc gaa ttc cca tat ctc gtg acc cct gag cag gct att caa    1344
Gly Thr Ala Glu Phe Pro Tyr Leu Val Thr Pro Glu Gln Ala Ile Gln
                435                 440                 445 gcc gag gtg ctc aag cat aag ggc agc gtc tac gcc atc acg gac aac    1392
Ala Glu Val Leu Lys His Lys Gly Ser Val Tyr Ala Ile Thr Asp Asn
450                 455                 460 tgg gcg ctg agc cag gtg gag acc ctc gct aaa caa gcc agt gtc tct    1440
Trp Ala Leu Ser Gln Val Glu Thr Leu Ala Lys Gln Ala Ser Val Ser
465                 470                 475                 480 ctt gta ttt gtc aac tcg gac gcg gga gag ggc tat atc tcc gtg gac    1488
Leu Val Phe Val Asn Ser Asp Ala Gly Glu Gly Tyr Ile Ser Val Asp
                485                 490                 495 gga aac gag ggc gac cgc aac aac ctc acc ctc tgg aag aac ggc gac    1536
Gly Asn Glu Gly Asp Arg Asn Asn Leu Thr Leu Trp Lys Asn Gly Asp
            500                 505                 510 aac ctc atc aag gct gct gca aac aac tgc aac aac acc atc gtt gtc    1584
Asn Leu Ile Lys Ala Ala Ala Asn Asn Cys Asn Asn Thr Ile Val Val
                515                 520                 525 atc cac tcc gtt gga cct gtt ttg gtt gac gag tgg tat gac cac ccc    1632
Ile His Ser Val Gly Pro Val Leu Val Asp Glu Trp Tyr Asp His Pro
        530                 535                 540 aac gtt act gcc atc ctc tgg gcg ggc ttg cct ggc cag gag tct ggc    1680
Asn Val Thr Ala Ile Leu Trp Ala Gly Leu Pro Gly Gln Glu Ser Gly
545                 550                 555                 560 aac tcc ttg gct gac gtg ctc tac ggc cgc gtc aac ccg ggc gcc aaa    1728
Asn Ser Leu Ala Asp Val Leu Tyr Gly Arg Val Asn Pro Gly Ala Lys
                565                 570                 575 tct cca ttc acc tgg ggc aag acg agg gag gcg tac ggg gat tac ctt    1776
Ser Pro Phe Thr Trp Gly Lys Thr Arg Glu Ala Tyr Gly Asp Tyr Leu
            580                 585                 590 gtc cgt gag ctc aac aac ggc aac gga gct ccc caa gat gat ttc tcg    1824
Val Arg Glu Leu Asn Asn Gly Asn Gly Ala Pro Gln Asp Asp Phe Ser
                595                 600                 605 gaa ggt gtt ttc att gac tac cgc gga ttc gac aag cgc aat gag acc    1872
Glu Gly Val Phe Ile Asp Tyr Arg Gly Phe Asp Lys Arg Asn Glu Thr
        610                 615                 620 ccg atc tac gag ttc gga cat ggt ctg agc tac acc act ttc aac tac    1920
Pro Ile Tyr Glu Phe Gly His Gly Leu Ser Tyr Thr Thr Phe Asn Tyr
625                 630                 635                 640 tct ggc ctt cac atc cag gtt ctc aac gct tcc tcc aac gct caa gta    1968
```

```
Ser Gly Leu His Ile Gln Val Leu Asn Ala Ser Ser Asn Ala Gln Val
                645                 650                 655 gcc act gag act ggc gcc gct ccc acc ttc gga caa gtc ggc aat gcc      2016
Ala Thr Glu Thr Gly Ala Ala Pro Thr Phe Gly Gln Val Gly Asn Ala
            660                 665                 670 tct gac tac gtg tac cct gag gga ttg acc aga atc agc aag ttc atc      2064
Ser Asp Tyr Val Tyr Pro Glu Gly Leu Thr Arg Ile Ser Lys Phe Ile
        675                 680                 685 tat ccc tgg ctt aat tcc aca gac ctg aag gcc tca tct ggc gac ccg      2112
Tyr Pro Trp Leu Asn Ser Thr Asp Leu Lys Ala Ser Ser Gly Asp Pro
    690                 695                 700 tac tat gga gtc gac acc gcg gag cac gtg ccc gag ggt gct act gat      2160
Tyr Tyr Gly Val Asp Thr Ala Glu His Val Pro Glu Gly Ala Thr Asp
705                 710                 715                 720 ggc tct ccg cag ccc gtt ctg cct gcc ggt ggt ggc tct ggt ggt aac      2208
Gly Ser Pro Gln Pro Val Leu Pro Ala Gly Gly Gly Ser Gly Gly Asn
                725                 730                 735 ccg cgc ctc tac gat gag ttg atc cgt gtt tcg gtg aca gtc aag aac      2256
Pro Arg Leu Tyr Asp Glu Leu Ile Arg Val Ser Val Thr Val Lys Asn
            740                 745                 750 act ggt cgt gtt gcc ggt gat gct gtg cct caa ttg tat gtt tcc ctt      2304
Thr Gly Arg Val Ala Gly Asp Ala Val Pro Gln Leu Tyr Val Ser Leu
        755                 760                 765 ggt gga ccc aat gag ccc aag gtt gtg ttg cgc aaa ttc gac cgc ctc      2352
Gly Gly Pro Asn Glu Pro Lys Val Val Leu Arg Lys Phe Asp Arg Leu
    770                 775                 780 acc ctc aag ccc tcc gag gag acg gtg tgg acg act acc ctg acc cgc      2400
Thr Leu Lys Pro Ser Glu Glu Thr Val Trp Thr Thr Thr Leu Thr Arg
785                 790                 795                 800 cgc gat ctg tct aac tgg gac gtt gcg gct cag gac tgg gtc atc act      2448
Arg Asp Leu Ser Asn Trp Asp Val Ala Ala Gln Asp Trp Val Ile Thr
                805                 810                 815 tct tac ccg aag aag gtc cat gtt ggt agc tct tcg cgt cag ctg ccc      2496
Ser Tyr Pro Lys Lys Val His Val Gly Ser Ser Ser Arg Gln Leu Pro
            820                 825                 830 ctt cac gcg gcg ctc ccg aag gtg caa tga                              2526
Leu His Ala Ala Leu Pro Lys Val Gln
        835                 840
```